(12) United States Patent
Chu et al.

(10) Patent No.: US 11,583,533 B2
(45) Date of Patent: Feb. 21, 2023

(54) TOPICAL PHARMACEUTICAL COMPOSITIONS COMPRISING 2-[3-[4-AMINO-3-(2-FLUORO-4-PHENOXY-PHENYL)-1H-PYRAZOLO[3,4-D]PYRIMIDIN-1-YL]PIPERIDINE-1-CARBONYL]-4,4-DIMETHYLPENT-2-ENENITRILE

(71) Applicant: Principia Biopharma Inc., South San Francisco, CA (US)

(72) Inventors: Katherine Chu, San Francisco, CA (US); Jyoti Wadhwa, San Mateo, CA (US); Jason Carbol, Petaluma, CA (US); Pasit Phiasivongsa, Hillsborough, CA (US); Claire Langrish, Redwood City, CA (US); Dolca Thomas, San Francisco, CA (US)

(73) Assignee: Principia Biopharma Inc., South San Francisco, CA (US)

( * ) Notice: Subject to any disclaimer, the term of this patent is extended or adjusted under 35 U.S.C. 154(b) by 0 days.

(21) Appl. No.: 17/143,384

(22) Filed: Jan. 7, 2021

(65) Prior Publication Data

US 2021/0205313 A1    Jul. 8, 2021

Related U.S. Application Data

(60) Provisional application No. 63/003,536, filed on Apr. 1, 2020, provisional application No. 62/958,616, filed on Jan. 8, 2020.

(51) Int. Cl.
*A61K 31/519* (2006.01)
*A61K 9/06* (2006.01)
(Continued)

(52) U.S. Cl.
CPC .............. *A61K 31/519* (2013.01); *A61K 9/06* (2013.01); *A61K 47/02* (2013.01); *A61K 47/10* (2013.01);
(Continued)

(58) Field of Classification Search
None
See application file for complete search history.

(56) References Cited

U.S. PATENT DOCUMENTS

| 8,673,925 B1 | 3/2014 | Goldstein |
| 8,946,241 B2 | 2/2015 | Goldstein |

(Continued)

FOREIGN PATENT DOCUMENTS

| WO | 2012158764 A1 | 11/2012 |
| WO | 2012158843 A2 | 11/2012 |

(Continued)

OTHER PUBLICATIONS

Ahmed, A., et al., "Magnitude of benefit for topical crisaborole in the treatment of atopic dermatitis in children and adults does not look promising: a critical appraisal," British Journal of Dermatology, vol. 178, pp. 659-662 (2018).

(Continued)

*Primary Examiner* — Melissa S Mercier
(74) *Attorney, Agent, or Firm* — McNeill Baur PLLC

(57) ABSTRACT

Disclosed herein are topical pharmaceutical compositions, e.g., for application to the skin of a subject, comprising (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (Compound (I)), methods of making the same, and methods of using the same, e.g., for the treatment of various dermatological disorders.

32 Claims, 8 Drawing Sheets

(51) Int. Cl.
| | |
|---|---|
| A61K 47/02 | (2006.01) |
| A61K 47/10 | (2017.01) |
| A61K 47/12 | (2006.01) |
| A61K 47/14 | (2017.01) |
| A61K 47/26 | (2006.01) |
| A61K 47/32 | (2006.01) |
| A61K 47/34 | (2017.01) |
| A61K 47/44 | (2017.01) |

(52) U.S. Cl.
CPC ............. *A61K 47/12* (2013.01); *A61K 47/14* (2013.01); *A61K 47/26* (2013.01); *A61K 47/32* (2013.01); *A61K 47/34* (2013.01); *A61K 47/44* (2013.01)

(56) References Cited

U.S. PATENT DOCUMENTS

| | | |
|---|---|---|
| 8,957,080 B2 | 2/2015 | Goldstein et al. |
| 8,962,635 B2 * | 2/2015 | Goldstein ............ A61K 9/2054 |
| | | 514/262.1 |
| 8,962,831 B2 | 2/2015 | Goldstein |
| 9,572,811 B2 | 2/2017 | Babler et al. |
| 9,580,427 B2 | 2/2017 | Taunton, Jr. et al. |
| 10,485,797 B2 | 11/2019 | Gourlay |
| 10,946,020 B2 | 3/2021 | Gourlay |
| 2017/0224688 A1 | 8/2017 | Krejsa |
| 2019/0231784 A1 | 8/2019 | Ferdous et al. |

FOREIGN PATENT DOCUMENTS

| | | |
|---|---|---|
| WO | 2013191965 A1 | 12/2013 |
| WO | 2014022569 A1 | 2/2014 |
| WO | 2014039899 A1 | 3/2014 |
| WO | 2016100914 A1 | 6/2016 |
| WO | 2022081512 A1 | 4/2022 |

OTHER PUBLICATIONS

Bennett, J.M., et al., "Inflammation—Nature's Way to Efficiently Respond to All Types of Challenges: Implications for Understanding and Managing "the Epidemic" of Chronic Diseases," Frontiers in Medicine (Lausanne), vol. 5, p. 316 (2018).
Bieber, T., "Atopic dermatitis," Annals of Dermatology, vol. 22, No. 2, pp. 125-137 (2010).
Bieber, T., et al., "Clinical phenotypes and endophenotypes of atopic dermatitis: Where are we, and where should we go?," Journal of Allergy Clinical Immunology, vol. 139, No. 4S, pp. S58-S64 (2017).
Bissonnette, R., et al., "Crisaborole and atopic dermatitis skin biomarkers: An intrapatient randomized trial," Journal of Allergy and Clinical Immunology, vol. 144, No. 5, pp. 1274-1289 (2019).
Bizikova, P., et al., "Cloning and establishment of canine desmocollin-1 as a major autoantigen in canine pemphigus foliaceus," Veterinary Immunology and Immunopathology, vol. 149, pp. 197-207 (2012).
Bizikova, P., et al., "Serum autoantibody profiles of IgA, IgE, and IgM in canine pemphigus foliaceus," Veterinary Dermatology, vol. 25, No. 5, p. 471 (2014).
Boguniewicz, M., et al, "Atopic dermatitis: a disease of altered skin barrier and immune dysregulation," Immunology Review, vol. 242, No. 1, pp. 233-246 (2011).
Boguniewicz, M., et al., "Expert Perspectives on Management of Moderate-to-Severe Atopic Dermatitis: A Multidisciplinary Consensus Addressing Current and Emerging Therapies," Journal of Allergy Clinical Immunology Practice, vol. 5, No. 6, pp. 1519-1531 (2017).
Byrd, J.C., et al., "Targeting BTK with Ibrutinib in Relapsed Chronic Lymphocytic Leukemia," New England Journal of Medicine, vol. 369, pp. 32-42 (2013).
Capen, C.C., "Mechanisms of chemical injury of the thyroid gland," Progress in Clinical and Biological Research, vol. 387, pp. 173-191 (1994), Abstract only.
Chang, B.Y., et al., "The Bruton tyrosine kinase inhibitor PCI-32765 ameliorates autoimmune arthritis by inhibition of multiple effector cells," Arthritis Research & Therapy, vol. 13, p. R115 (2011).
Crofford, L.J., et al., "The role of Bruton's tyrosine kinase in autoimmunity and implications for therapy," Expert Review of Clinical Immunology, vol. 12, No. 7, pp. 763-773 (2016).
Curran, P.G., et al., "The effect of hepatic enzyme-inducing drugs on thyroid hormones and the thyroid gland," Endocrinology, vol. 12, No. 2, pp. 135-150 (1991).
Di Paolo, J.A., et al., "Specific Btk inhibition suppresses B cell- and myeloid cell-mediated arthritis," Nature Chemical Biology, vol. 7, pp. 41-50 (2011).
Eichenfield, L.F., et al., "Guidelines of care for the management of atopic dermatitis: section 2. Management and treatment of atopic dermatitis with topical therapies," Journal of the American Academy of Dermatology, vol. 71, No. 1, pp. 116-132 (2014).
Futatani, T., et al., "Brutons tyrosine kinase is present in normal platelets and its absence identifies patients with X-linked agammaglobulinaemia and carrier females," British Journal of Hematology, vol. 114, No. 1, pp. 141-149 (2001).
Goodale, E.C., et al., "Efficacy of a Bruton's Tyrosine Kinase Inhibitor (PRN-473) in the treatment of canine pemphigus foliaceus," Veterinary Dermatology, vol. 31, No. 4, p. 291 (2020).
Hanifin, J.M., et al., "Diagnostic features of atopic dermatitis," Acta Dermato-Venereologica Supplement (Stockholm), vol. 92, pp. 44-47 (1980).
Herter, J.M., et al., "PRN473, an inhibitor of Bruton's tyrosine kinase, inhibits neutrophil recruitment via inhibition of macrophage antigen-1 signalling," British Journal of Pharmacology, vol. 175, No. 3, pp. 429-439 (2018).
Honigberg, L.A., et al., "The Bruton tyrosine kinase inhibitor PCI-32765 blocks B cell activation and is efficacious in models of autoimmune disease and B cell malignancy," PNAS, vol. 107, pp. 13075-13080 (2010).
Hutcheson, J., et al., "Modulating proximal cell signaling by targeting Btk ameliorates humoral autoimmunity and endorgan disease in murine lupus," Arthritis Research & Therapy, vol. 14, p. R243 (2012).
Ihrke, P.J., et al., "Pemphigus foliaceus in dogs: a review of 37 cases," Journal of the American Veterinary Medical Association, vol. 186, No. 1, pp. 59-66 (1985), Abstract only.
International Preliminary Report on Patentability issued for PCT/US2021/012507 dated Jul. 21, 2022 (9 pages).
Irwin, S., "Comprehensive observational assessment: la. A systematic, quantitative procedure for assessing the behavioral and physiologic state of the mouse," Psychopharmacologia, vol. 13, No. 3, pp. 222-257 (1968).
Kim, K.H., et al., "Imidazo[1,5-a]quinoxalines as irreversible BTK inhibitors for the treatment of rheumatoid arthritis," Bioorganic & Medicinal Chemistry Letters, vol. 21, No. 21, pp. 6258-6263 (2011).
Lebakken, C.S., et al., "Development and application of a broad-coverage, TR-FRET-based kinase binding assay platform," Journal of Biomolecular Screening, vol. 14, pp. 924-935 (2009).
Maronpot, R.R., et al., "Hepatic Enzyme Induction: Histopathology," Toxicologic Pathology, vol. 38, No. 5, pp. 776-795 (2010).
Mohamed, A.J., et al., "Bruton's tyrosine kinase (Btk): function, regulation, and transformation with special emphasis on the PH domain," Immunology Review, vol. 228, pp. 58-73 (2009).
Oliveira, S., et al., "Neutrophil migration in infection and wound repair: going forward in reverse," Nature Reviews Immunology, vol. 16, No. 6, pp. 378-391 (2016).
Outerbridge, C., et al., A New Treatment for Autoimmune Blistering Diseases: Efficacy of the Bruton's Tyrosine Kinase (BTK) Inhibitor PRN473 in Canine *Pemphigus foliaceus*, Poster #3530, 74th Annual Meeting, American Academy of Dermatology (AAD), Washington, D.C., Mar. 2016.

(56) References Cited

OTHER PUBLICATIONS

Patel, K.R., et al., "Association between atopic dermatitis, depression, and suicidal ideation: A systematic review and meta-analysis," Journal of the American Academy of Dermatology, vol. 80, No. 2, pp. 402-410 (2019).

Petersen, L.J., et al., "Histamine is released in the wheal but not the flare following challenge of human skin in vivo: a microdialysis study," Clinical & Experimental Allergy, vol. 27, No. 3, pp. 284-329 (1997).

Press Release, "Sanofi to acquire Principia Biopharma," Aug. 17, 2020.

Rip, J., et al., "The role of Bruton's Tyrosine Kinase in immune cell signaling and systemic autoimmunity," Critical Reviews in Immunology, vol. 38, No. 1, pp. 17-62 (2018).

Sideras, P., et al., "Molecular and cellular aspects of X-linked agammaglobulinemia," Advanced Immunology, vol. 59, pp. 135-223 (1995).

Silverberg, J.I., "Public Health Burden and Epidemiology of Atopic Dermatitis," Dermatologic Clinics, vol. 35, No. 3, pp. 283-289 (2017).

Silverberg, J.I., "Selected comorbidities of atopic dermatitis: Atopy, neuropsychiatric, and musculoskeletal disorders," Clinical Dermatology, vol. 35, No. 4, pp. 360-366 (2017).

Silverberg, J.I., et al., "Patient burden and quality of life in atopic dermatitis in US adults: A population-based cross-sectional study," Annals of Allergy, Asthma & Immunology, vol. 121, No. 3, pp. 340-347 (2018).

Spiewak, R., "Inter- and intra-individual variability of skin reactivity to histamine at prick-testing," Dermatology Online Journal, vol. 1, No. 1 (1995).

Trial Registration No. ACTRN12613000951752, "A Phase I, Randomised, Double-Blind, Placebo-Controlled, Ascending Single- and Repeat-Dose Study of the Safety, Tolerability and Pharmacokinetics of Orally Administered PRN473," Australian New Zealand Clinical Trials Registry, Aug. 27, 2013.

Trial Registration No. ACTRN12620000264298, "A Healthy Volunteer Study Evaluating the Tolerability and Pharmacokinetics of PRN473 Topical," Australian New Zealand Clinical Trials Registry, Feb. 28, 2020.

Trial Registration No. ACTRN12620000693921, "An interventional study to evaluate the effect and safety of PRN473 topical on skin reactions of otherwise healthy participants with allergies to common allergens," Australian New Zealand Clinical Trials Registry, Jun. 22, 2020.

Volmering, S., et al., "The Neutrophil Btk Signalosome Regulates Integrin Activation during Sterile Inflammation," Immunity, vol. 44, No. 1, pp. 73-87 (2016).

Weidinger, S., et al., "Atopic dermatitis," Nature Reviews Disease Primers, vol. 4, No. 1, p. 1 (2018).

Werfel, T., et al., "Cellular and molecular immunologic mechanisms in patients with atopic dermatitis," Journal of Allergy and Clinical Immunology, vol. 138, No. 2, pp. 336-349 (2016).

Xu, D., et al. "RN486, a selective Bruton's tyrosine kinase inhibitor, abrogates immune hypersensitivity responses and arthritis in rodents," Journal of Pharmacology and Experimental Therapeutics, vol. 341, pp. 90-103 (2012).

Zane, L.T., et al., "Tolerability of crisaborole ointment for application on sensitive skin areas: A randomized, double-blind, vehicle-controlled study in healthy volunteers," American Journal of Clinical Dermatology, vol. 17, pp. 519-526 (2016).

\* cited by examiner

TOPICAL PHARMACEUTICAL COMPOSITIONS COMPRISING 2-[3-[4-AMINO-3-(2-FLUORO-4-PHENOXY-PHENYL)-1H-PYRAZOLO[3,4-D]PYRIMIDIN-1-YL]PIPERIDINE-1-CARBONYL]-4,4-DIMETHYLPENT-2-ENENITRILE

This application claims the benefit of priority to U.S. Provisional Application No. 62/958,616, filed Jan. 8, 2020, and U.S. Provisional Application No. 63/003,536, filed Apr. 1, 2020, the contents of each of which are incorporated by referenced herein in their entirety.

The present disclosure is directed to topical pharmaceutical compositions comprising 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (Compound (I), also known as PRN473) or a pharmaceutically acceptable salt thereof, and methods of using the same, e.g., in treating various dermatological disorders.

Compound (I) is an inhibitor of Bruton's tyrosine kinase (BTK). The enzyme BTK is a member of the Tec family non-receptor tyrosine kinases. BTK is expressed in most hematopoietic cells, including B cells, mast cells, and macrophages. BTK plays a role in the development and activation of B cells. BTK activity has been implicated in the pathogenesis of several disorders and conditions, such as B cell-related hematological cancers (e.g., non-Hodgkin lymphoma and B cell chronic lymphocytic leukemia) and autoimmune diseases (e.g., rheumatoid arthritis, Sjogren's syndrome, pemphigus, IBD, lupus, and asthma).

Compound (I), pharmaceutically acceptable salts thereof, and various solid forms of any of the foregoing may inhibit BTK and be useful in the treatment of disorders and conditions mediated by BTK activity, including various dermatological disorders. Compound (I) is disclosed as, e.g., Compound 125A/125B in Table 1 of WO 2012/158764 and has the following structure:

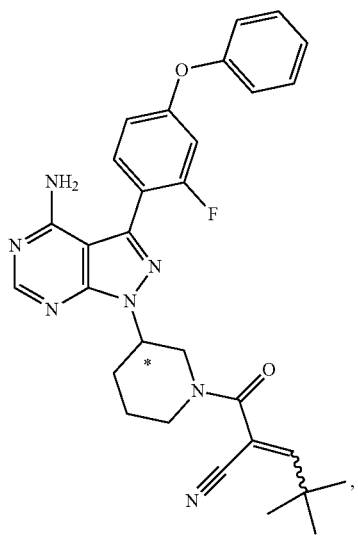 [SMILES: CC(C)(C)C=C(C#N)C(=O)N1CCCC(n2nc(-c3ccc(Oc4ccccc4)cc3F)c3c(N)ncnc32)C1]

where *C is a stereochemical center.

Topical pharmaceutical compositions are useful for treating various dermatologic disorders. These formulations enable local delivery of an active pharmaceutical ingredient (API), potentially improving efficacy and reducing adverse effects associated with systemic administration of the API. However, many active pharmaceutical ingredients are difficult to formulate as suspensions or solutions (e.g., gels, ointments, or creams) suitable for application to the skin of a patient suffering from a dermatologic disorder. Illustratively, some APIs exhibit insufficient chemical and physical stability in topical formulations, reducing their shelf-life and safety profile.

Stable topical formulations may enhance shelf-life and offer better chemical and physical stability and, in some embodiments, better efficacy, particularly in the treatment of dermatologic disorders using BTK inhibitors such as Compound (I). Accordingly, there is a need in the art for stable topical formulations comprising Compound (I) or a pharmaceutically acceptable salt thereof. Such formulations may be useful in the treatment of dermatologic disorders including, but not limited to, pemphigus vulgaris, pemphigus *foliaceus*, cutaneous lupus, cutaneous lupus erythematosus, dermatitis, discoid lupus, atopic dermatitis, bullous pemphigoid, drug related skin reaction, chronic idiopathic urticaria, chronic spontaneous urticaria, symptomatic dermographism, alopecia, alopecia areata, vitiligo, pyoderma gangrenosum, membrane pemphigoid, epidermolysis bullosa acquisita, Steven Johnson Syndrome, TEN Toxic epidermal necrolysis, drug eruptions, folliculitis decalvans, pseudofolliculitis barbae, leukocytoclastic vasculitis, hidradenitis suppurativa, palmar plantar pustulosis, Lichenoid dermatitis, dermatitis herpetiformis, rosacea, erythema of rosacea, papulopustular rosacea, neutrophilic dermatoses, chronic kidney disease associated pruritus, end stage renal disease induced pruritis, acne, mycosis fungoides, and sweet syndrome.

Disclosed herein are novel topical pharmaceutical compositions comprising Compound (I) or a pharmaceutically acceptable salt thereof and methods of using and making the same. In some embodiments, the topical pharmaceutical compositions are used to treat a subject suffering from a dermatologic disorder, e.g., by applying the composition to at least a portion of the skin of the subject.

In some embodiments, the present disclosure provides a topical pharmaceutical composition for application to the skin of a subject, the topical pharmaceutical composition comprising:

a compound chosen from (E) isomer, (Z) isomer, and a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (Compound (I)), or a pharmaceutically acceptable salt of any of the foregoing; and at least one pharmaceutically acceptable excipient, wherein the composition is in a form chosen from suspensions, solutions, and combinations thereof.

In some embodiments, Compound (I) or the pharmaceutically acceptable salt thereof is micronized. In some embodiments, Compound (I) or the pharmaceutically acceptable salt thereof has a particle size distribution $D_{90}$ ranging from about 5 to about 10 microns.

In some embodiments, the compound is Compound (I).

In some embodiments, the compound is an amorphous form of Compound (I).

In some embodiments, the compound is a crystalline form of Compound (I). In some embodiments, the compound is crystalline Form (I) of Compound (I). In some embodiments, the compound is crystalline Form (II) of Compound (I).

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, at least about 95% by weight of Compound (I) is the (E) isomer.

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and at least about 95% by weight of Compound (I) is the (E) isomer.

In some embodiments, the topical pharmaceutical composition is in the form of a suspension.

In some embodiments, the topical pharmaceutical compositions is in a form chosen from gels, ointments, and creams.

In some embodiments, the present disclosure provides a topical pharmaceutical composition for application to the skin of a subject, wherein the topical pharmaceutical composition is in the form a suspension comprising:

a compound chosen from (E) isomer, (Z) isomer, and a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (Compound (I)), or a pharmaceutically acceptable salt thereof; and at least one pharmaceutically acceptable excipient, wherein the at least one pharmaceutically acceptable excipient comprises:
  a vehicle;
  a humectant and/or an emollient;
  a wetting agent; and
  a thickener.

In some embodiments, Compound (I) or the pharmaceutically acceptable salt thereof is micronized. In some embodiments, Compound (I) or the pharmaceutically acceptable salt thereof has a particle size distribution $D_{90}$ ranging from 5 to 10 microns.

In some embodiments, the compound is Compound (I).

In some embodiments, the compound is an amorphous form of Compound (I).

In some embodiments, the compound is a crystalline form of Compound (I). In some embodiments, the compound is crystalline Form (I) of Compound (I). In some embodiments, the compound is crystalline Form (II) of Compound (I).

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, at least about 95% by weight of Compound (I) is the (E) isomer. In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and at least about 95% by weight of Compound (I) is the (E) isomer.

In some embodiments, the vehicle does not individually or in combination substantially dissolve Compound (I) or the pharmaceutically acceptable salt thereof. In some embodiments, the vehicle is chosen from water, mineral oil, and combinations thereof.

In some embodiments, the humectant and/or the emollient retains Compound (I) or the pharmaceutically acceptable salt thereof on the skin, e.g., retains an amount of Compound (I) or the pharmaceutically acceptable salt thereof on at least a portion of the skin of a subject. the humectant and/or emollient comprises at least one component chosen from propylene glycol, glycerin, medium chain triglycerides, and combinations of any of the foregoing.

In some embodiments, the wetting agent keeps Compound (I) or the pharmaceutically acceptable salt thereof de-agglomerated, e.g., the wetting agent reduces the amount of agglomeration relative to a substantially similar formulation that does not contain the wetting agent. In some embodiments, the wetting agent comprises at least one component chosen from polyethoxylated sorbitan and oleic acid (Polysorbate 80), dimethicone (polydimethylsiloxane), and combinations thereof.

In some embodiments, the thickener comprises at least one component chosen from crosslinked polyacrylic acid polymers (Carbopol® polymers), hydrogenated castor oils, microcrystalline waxes, and combinations of any of the foregoing.

In some embodiments, the at least one pharmaceutically acceptable excipient comprises:
  a vehicle chosen from water, mineral oil, and combinations thereof;
  a humectant and/or an emollient comprising at least one component chosen from propylene glycol, glycerin, medium chain triglycerides, and combinations of any of the foregoing;
  a wetting agent comprising at least one component chosen from polyethoxylated sorbitan and oleic acid (Polysorbate 80), dimethicone (polydimethylsiloxane), and combinations thereof; and
  a thickener comprising at least one component chosen from crosslinked polyacrylic acid polymers (Carbopol® polymers), hydrogenated castor oils, microcrystalline waxes, and combinations of any of the foregoing.

In some embodiments, the topical pharmaceutical composition comprises:
  about 0.1% to about 10% by weight of Compound (I) or a pharmaceutically acceptable salt thereof;
  about 0.1% to about 20% by weight of medium-chain triglycerides;
  about 0.1% to about 20% by weight of polyethoxylated sorbitan and oleic acid (Polysorbate 80);
  about 0.1% to about 20% by weight of natural glycerin;
  about 0.1% to about 45% by weight of propylene glycol;
  about 0.01% to about 0.5% by weight of methylparaben;
  about 0.01% to about 0.2% by weight of propylparaben;
  about 0.1% to about 4% by weight of a crosslinked polyacrylic acid polymer;
  an amount of about 10% (w/w) of sodium hydroxide solution; and
  Q. S. to 100 of water.

In some embodiments, the crosslinked polyacrylic acid polymer is Carbopol® 980 polymer.

In some embodiments, the amount of 10% (w/w) sodium hydroxide solution is sufficient to adjust the pH of the topical pharmaceutical composition to a value in the range of about 3.5 to about 8.5.

In some embodiments, Compound (I) or the pharmaceutically acceptable salt thereof is present in the topical pharmaceutical composition in an amount of about 0.1%, about 0.5%, about 2%, about 5%, or about 10%, by weight of the composition.

In some embodiments, the compound is Compound (I).

In some embodiments, the compound is an amorphous form of Compound (I).

In some embodiments, the compound is a crystalline form of Compound (I). In some embodiments, the compound is crystalline Form (I) of Compound (I). In some embodiments, the compound is crystalline Form (II) of Compound (I).

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, at least about 95% by weight of Compound (I) is the (E) isomer. In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and at least about 95% by weight of Compound (I) is the (E) isomer.

In some embodiments, the topical pharmaceutical composition comprises:
  about 0.1%, about 0.5%, about 2%, about 5%, or about 10% by weight of Compound (I) or a pharmaceutically acceptable salt thereof;
  about 2% by weight of medium-chain triglycerides;
  about 2% by weight of polyethoxylated sorbitan and oleic acid (Polysorbate 80);
  about 5% by weight of natural glycerin;
  about 10% by weight of propylene glycol;
  about 0.20% by weight of methylparaben;
  about 0.05% by weight of propylparaben;
  about 0.75% by weight of a crosslinked polyacrylic acid polymer;
  an amount of 10% (w/w) of sodium hydroxide solution; and
  Q.S. to 100 of water.

In some embodiments, the crosslinked polyacrylic acid polymer is Carbopol® 980 polymer.

In some embodiments, the amount of 10% (w/w) sodium hydroxide solution is sufficient to adjust the pH of the topical pharmaceutical composition to a value in the range of about 4.5 to about 5.5.

In some embodiments, the topical pharmaceutical composition is in the form of a gel.

In some embodiments, the compound is Compound (I).

In some embodiments, the compound is an amorphous form of Compound (I).

In some embodiments, the compound is a crystalline form of Compound (I). In some embodiments, the compound is crystalline Form (I) of Compound (I). In some embodiments, the compound is crystalline Form (II) of Compound (I).

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, at least about 95% by weight of Compound (I) is the (E) isomer.

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and at least about 95% by weight of Compound (I) is the (E) isomer.

In some embodiments, the topical pharmaceutical composition comprises:
  about 0.1% to about 10% by weight of Compound (I) or a pharmaceutically acceptable salt thereof;
  about 0.1% to about 20% by weight of medium-chain triglycerides;
  about 0.1% to about 20% by weight of microcrystalline wax;
  about 0.1% to about 10% by weight of hydrogenated castor oil;
  about 0.01% to about 10% by weight of dimethicone; and
  Q.S. to 100 of white mineral oil.

In some embodiments, the dimethicone has a viscosity of 12500 centistokes (cSt).

In some embodiments, the white mineral oil is Kaydol White Mineral Oil.

In some embodiments, Compound (I) or the pharmaceutically acceptable salt thereof is present in an amount of about 0.1%, about 0.5%, about 2%, about 5% or about 10%, by weight of the composition.

In some embodiments, the compound is Compound (I).

In some embodiments, the compound is an amorphous form of Compound (I).

In some embodiments, the compound is a crystalline form of Compound (I). In some embodiments, the compound is crystalline Form (I) of Compound (I). In some embodiments, the compound is crystalline Form (II) of Compound (I).

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, at least about 95% by weight of Compound (I) is the (E) isomer.

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and at least about 95% by weight of Compound (I) is the (E) isomer.

In some embodiments, the topical pharmaceutical composition comprises:
  about 0.1%, about 0.5%, about 2%, about 5%, or about 10% by weight of Compound (I) or a pharmaceutically acceptable salt thereof;
  about 2% by weight of medium-chain triglycerides;
  about 2% to about 20% by weight of polyethoxylated sorbitan and oleic acid (Polysorbate 80);
  about 5% by weight of natural glycerin;
  about 10% by weight of propylene glycol;
  about 0.20% by weight of methylparaben;
  about 0.05% by weight of propylparaben;
  about 0.75% by weight of a crosslinked polyacrylic acid polymer;
  an amount of 10% (w/w) sodium hydroxide solution; and
  Q.S. to 100 of water.

In some embodiments, the crosslinked polyacrylic acid polymer is Carbopol® 980 polymer.

In some embodiments, the amount of 10% (w/w) sodium hydroxide solution is sufficient to adjust the pH of the topical pharmaceutical composition to a value in the range of about 4.5 to about 5.5.

In some embodiments, the topical pharmaceutical composition is in the form of a gel.

In some embodiments, the compound is Compound (I).

In some embodiments, the compound is an amorphous form of Compound (I).

In some embodiments, the compound is a crystalline form of Compound (I). In some embodiments, the compound is crystalline Form (I) of Compound (I). In some embodiments, the compound is crystalline Form (II) of Compound (I).

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, at least about 95% by weight of Compound (I) is the (E) isomer.

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and at least about 95% by weight of Compound (I) is the (E) isomer.

In some embodiments, the topical pharmaceutical composition comprises:
  about 0.1% to about 10% by weight of Compound (I) or a pharmaceutically acceptable salt thereof;
  about 0.1% to about 20% by weight of medium-chain triglycerides;
  about 0.1% to about 20% by weight of microcrystalline wax;
  about 0.1% to about 10% by weight of hydrogenated castor oil;
  about 0.01% to about 10% by weight of dimethicone; and
  Q.S. to 100 of a mineral oil.

In some embodiments, the dimethicone has a viscosity of 12500 centistokes (cSt).

In some embodiments, Compound (I) or the pharmaceutically acceptable salt thereof in the topical pharmaceutical composition is present in an amount of about 0.1%, about 0.5%, about 2%, about 5%, or about 10%, by weight of the composition.

In some embodiments, the compound is Compound (I).

In some embodiments, the compound is an amorphous form of Compound (I).

In some embodiments, the compound is a crystalline form of Compound (I). In some embodiments, the compound is crystalline Form (I) of Compound (I). In some embodiments, the compound is crystalline Form (II) of Compound (I).

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, at least about 95% by weight of Compound (I) is the (E) isomer.

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and at least about 95% by weight of Compound (I) is the (E) isomer.

In some embodiments, the topical pharmaceutical composition comprises:
  about 0.1%, about 0.5%, about 2%, about 5%, or about 10%, by weight of Compound (I) or a pharmaceutically acceptable salt thereof;
  about 10% by weight of medium-chain triglycerides;
  about 5% by weight of microcrystalline wax;
  about 2% by weight of hydrogenated castor oil;
  about 3% by weight of dimethicone; and
  Q.S. to 100 of a mineral oil.

In some embodiments, the topical pharmaceutical composition is in the form of an ointment.

In some embodiments, the compound is Compound (I).

In some embodiments, the compound is an amorphous form of Compound (I).

In some embodiments, the compound is a crystalline form of Compound (I). In some embodiments, the compound is crystalline Form (I) of Compound (I). In some embodiments, the compound is crystalline Form (II) of Compound (I).

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, at least about 95% by weight of Compound (I) is the (E) isomer.

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and at least about 95% by weight of Compound (I) is the (E) isomer.

In some embodiments, the present disclosure provides a topical pharmaceutical composition in the form of a cream for application to the skin of a subject, the composition comprising:
  about 0.01% to about 2% by weight of Compound (I) or a pharmaceutically acceptable salt thereof;
  about 1% to about 45% by weight of oleic acid;
  about 0.1% to about 20% by weight of glycerin;
  about 0.1% to about 45% by weight of propylene glycol;
  about 0.1% to about 5% by weight of benzyl alcohol;
  about 0.1% to about 5% by weight of high molecular weight copolymers of acrylic acid and $C_{10}$-$C_{30}$ alkyl acrylate crosslinked with allyl pentaerythritol (a Pemulen™ polymer);
  an amount of 10% (w/w) sodium hydroxide solution sufficient to adjust the pH to about 3.5 to about 8.5; and
  Q.S. to 100 of water.

In some embodiments, the high molecular weight copolymers of acrylic acid and $C_{10}$-$C_{30}$ alkyl acrylate crosslinked with allyl pentaerythritol (a Pemulen™ polymer) is Pemulen™ TR-1.

In some embodiments, the compound is Compound (I).

In some embodiments, the compound is an amorphous form of Compound (I).

In some embodiments, the compound is a crystalline form of Compound (I). In some embodiments, the compound is crystalline Form (I) of Compound (I). In some embodiments, the compound is crystalline Form (II) of Compound (I).

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, at least about 95% by weight of Compound (I) is the (E) isomer.

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and at least about 95% by weight of Compound (I) is the (E) isomer.

In some embodiments, the topical pharmaceutical composition in the form of a cream comprises:
  about 0.2% by weight of Compound (I) or a pharmaceutically acceptable salt thereof;
  about 25% by weight of oleic acid;
  about 5% by weight of glycerin;
  about 5% by weight of propylene glycol;
  about 1% by weight of benzyl alcohol;
  about 0.75% by weight of Pemulen™ TR-1 polymer;
  an amount of 10% (w/w) sodium hydroxide solution; and
  Q.S. to 100 of water.

In some embodiments, the amount of 10% (w/w) sodium hydroxide solution is sufficient to adjust the pH of the topical pharmaceutical composition to a value in the range of about 4.5 to about 5.5.

In some embodiments, the compound is Compound (I).

In some embodiments, the compound is an amorphous form of Compound (I).

In some embodiments, the compound is a crystalline form of Compound (I). In some embodiments, the compound is crystalline Form (I) of Compound (I). In some embodiments, the compound is crystalline Form (II) of Compound (I).

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, at least about 95% by weight of Compound (I) is the (E) isomer.

In some embodiments, at least about 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and at least about 95% by weight of Compound (I) is the (E) isomer.

DEFINITIONS

Figure 1:
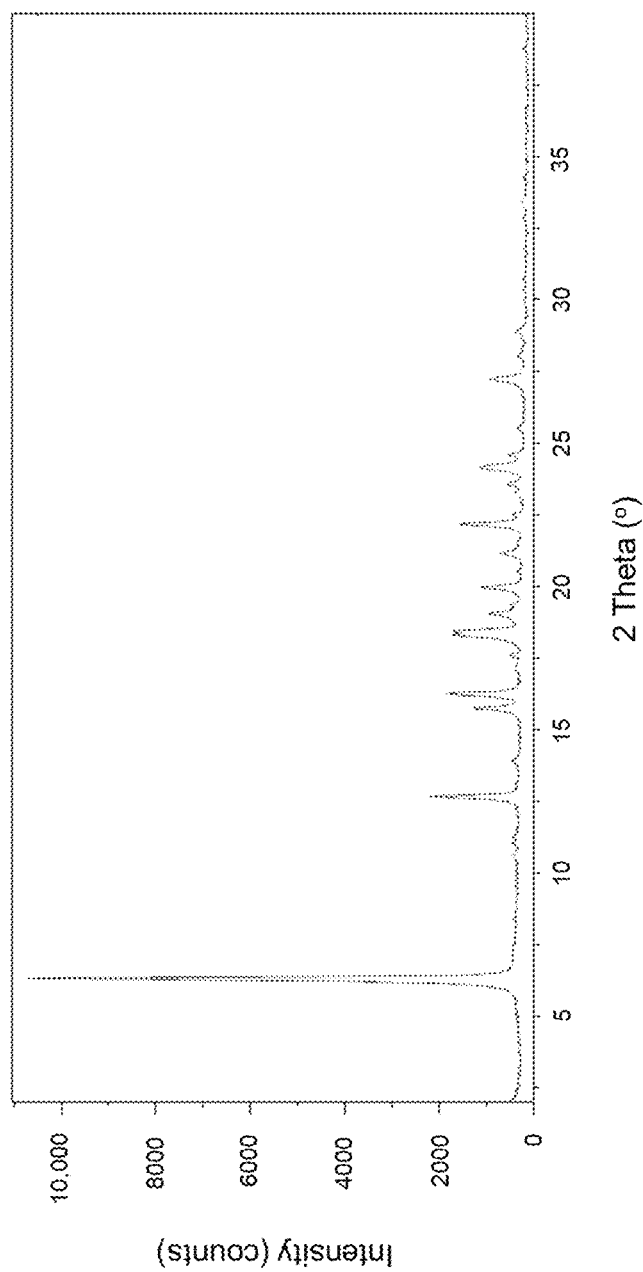
FIG. 1 shows an X-ray powder diffractogram for crystalline Form (I) of Compound (I), referred to as crystalline Form (I) herein, showing degrees 2θ (2-theta) on the X-axis and relative intensity on the Y-axis.

As used herein, "a" or "an" entity refers to one or more of that entity, e.g., "a compound" refers to one or more compounds or at least one compound unless stated otherwise. As such, the terms "a" (or "an"), "one or more", and "at least one" are used interchangeably herein.

As used herein, the term "about" or "approximately" means approximately, in the region of, roughly, or around. When the term "about" is used in conjunction with a numerical range, it modifies that range by extending the boundaries above and below the numerical values set forth.

In general, the term "about" is used herein to modify a numerical value above and below the stated value by a variance of 5%.

As used herein, "Compound (I)" refers to the (E) isomer, (Z) isomer, or a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, (S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, or a mixture of (R) and (S) enantiomers of 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, which has the following structure:

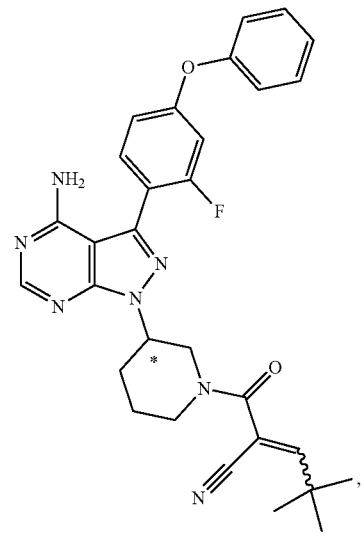 [SMILES: CC(C)(C)C=C(C#N)C(=O)N1CCCC(n2nc(-c3ccc(Oc4ccccc4)cc3F)c3c(N)ncnc32)C1]

where *C is a stereochemical center.

When Compound (I) is denoted as (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, it may contain the corresponding (S) enantiomer as an impurity in less than 1% by weight, or an impurity in less than 5% by weight. Accordingly, when the Compound (I) is denoted as a mixture of (R) and (S) enantiomers of 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, the amount of (R) or (S) enantiomer in the mixture is greater than 1% by weight. Similarly, when Compound (I) is denoted as the (E) isomer, it may contain the corresponding (Z) isomer as an impurity in less than 1% by weight. Accordingly, when the Compound (I) is denoted as a mixture of (E) and (Z) isomers of 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, the amount of (E) or (Z) isomer in the mixture is greater than 1% by weight.

In some embodiments, Compound (I) is a mixture of (R) and (S) enantiomers of 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, Compound (I) is substantially (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile. In some embodiments, Compound (I) is at least about 75%, e.g., at least about 80%, at least about 85%, at least about 90%, at least about 95%, by weight (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile. In some embodiments, Compound (I) is at least about 95% by weight (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

Herein, Compound (I) may be referred to as a "drug," "active agent," "a therapeutically active agent," or a "API."

As used herein, the term "solution" with regard to the form of a topical pharmaceutical composition includes emulsions wherein the API is dissolved in a vehicle.

As used herein, the term "suspension" with regard to the form of a topical pharmaceutical composition includes formulations wherein the API is dispersed/suspended in a vehicle.

As used herein, "substantially pure" in connection with a geometric isomeric form refers to a compound, such as Compound (I), wherein more than 70% by weight or moles of the compound is present as the given isomeric form. For example, the phrase "Compound (I) is a substantially pure (E) isomer" refers to Compound (I) having at least 70% by weight or moles of the (E) isomeric form, and the phrase "Compound (I) is a substantially pure (Z) isomer" refers to Compound (I) having at least 70% by weight or moles the (Z) isomeric form. In some embodiments, at least 80% by weight or moles of Compound (I) is the (E) form or at least 80% by weight or moles of Compound (I) is the (Z) form. In some embodiments, at least 85% by weight or moles of Compound (I) is in the (E) form or at least 85% by weight or moles of Compound (I) is in the (Z) form. In some embodiments, at least 90% by weight or moles of Compound (I) is in the (E) form or at least 90% by weight or moles of Compound (I) is in the (Z) form. In some embodiments, at least 95% by weight or moles of Compound (I) is in the (E) form or at least 95% by weight or moles of Compound (I) is in the (Z) form. In some embodiments, at least 97% by weight or moles, or 98% by weight or moles, of Compound (I) is in the (E) form or at least 97% by weight or moles, or 98% by weight or moles, of Compound (I) is in the (Z) form. In some embodiments, at least 99% by weight or moles of Compound (I) is in the (E) form or at least 99% by weight or moles of Compound (I) is in the (Z) form. The relative amounts of (E) and (Z) isomers in a solid mixture can be determined according to standard methods and techniques known in the art.

In some embodiments, Compound (I) is a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, Compound (I) is a substantially pure (E) isomer of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile. In some embodiments, Compound (I) is at least about 75%, e.g., at least about 80%, at least about 85%, at least about 90%, at least about 95%, by weight (E) isomer of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile. In some embodiments, Compound (I) is at least about 95% by weight (E) isomer of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

As used herein, the term "pharmaceutically acceptable salt" refers to a non-toxic salt form of a compound of this disclosure. Pharmaceutically acceptable salts of Compound (I) of this disclosure include those derived from suitable inorganic and organic acids and bases. Pharmaceutically acceptable salts are well known in the art. Suitable pharmaceutically acceptable salts are, e.g., those disclosed in Berge, S. M., et al. J. Pharma. Sci. 66:1-19 (1977). Non-limiting examples of pharmaceutically acceptable salts disclosed in that article include: acetate; benzenesulfonate; benzoate; bicarbonate; bitartrate; bromide; calcium edetate; camsylate; carbonate; chloride; citrate; dihydrochloride; edetate; edisylate; estolate; esylate; fumarate; gluceptate; gluconate; glutamate; glycollylarsanilate; hexylresorcinate; hydrabamine; hydrobromide; hydrochloride; hydroxynaphthoate; iodide; isethionate; lactate; lactobionate; malate; maleate; mandelate; mesylate; methylbromide; methylnitrate; methyl sulfate; mucate; napsylate; nitrate; pamoate (embonate); pantothenate; phosphate/diphosphate; polygalacturonate; salicylate; stearate; subacetate; succinate; sulfate; tannate; tartrate; teociate; triethiodide; benzathine; chloroprocaine; choline; diethanolamine; ethylenediamine; meglumine; procaine; aluminum; calcium; lithium; magnesium; potassium; sodium; and zinc.

Non-limiting examples of pharmaceutically acceptable salts derived from appropriate acids include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Additional non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Non-limiting examples of pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other non-limiting examples of pharmaceutically acceptable salts include besylate and glucosamine salts.

As used herein, a "pharmaceutically acceptable excipient" refers to a carrier or an excipient that is useful in preparing a pharmaceutical composition. For example, a pharmaceutically acceptable excipient is generally safe and includes carriers and excipients that are generally considered acceptable for mammalian pharmaceutical use.

As used herein, the term "inhibit," "inhibition," or 'inhibiting" refers to the reduction or suppression of a given condition, symptom, or disorder, or disease, or a significant decrease in the baseline activity of a biological activity or process.

As used herein, the term "treat," "treating," or "treatment," when used in connection with a disorder or condition, includes any effect, e.g., lessening, reducing, modulating, ameliorating, or eliminating, that results in the improvement of the disorder or condition. Improvements in or lessening the severity of any symptom of the disorder or condition can be readily assessed according to standard methods and techniques known in the art.

As used herein, a "mammal" refers to domesticated animals (e.g., dogs, cats, and horses) and humans. In some embodiments, the mammal is a human.

As used herein, the term "DSC" refers to the analytical method of differential scanning calorimetry.

As used herein, the term "TGA" refers to the analytical method of thermo gravimetric (also referred to as thermogravimetric) analysis.

As used herein, particle sizes are expressed in terms of particle size distribution (PSD) (e.g., $D_{10}$, $D_{50}$, and $D_{90}$ values). Particle size distribution may be affected by the hydration state of the particles. Illustratively, a wet particle size distribution may differ from a dry particle size distribution and corresponding possess different characteristic $D_{10}$, $D_{50}$, and $D_{90}$ values.

As would be understood by a person having ordinary skill in the art, particle sizes and particle size distributions of powders can be measured using various techniques known in the art, such as laser diffraction. In some embodiments, particle size distributions of solid forms of Compound (I) are expressed using values (e.g., $D_{10}$, $D_{50}$, and $D_{90}$ values) measured by laser diffraction.

As used herein, "$D_{50}$" refers to the median diameter of a particle size distribution. As used herein, "$D_{10}$" refers to the particle diameter at which 10% of a population of particles possess a particle diameter of $D_{10}$ or less.

As used herein, "$D_{90}$" refers to the particle diameter at which 90% of a population of particles possess a particle diameter of $D_{90}$ or less.

Example Embodiments 1

Non-limiting embodiments of the disclosure include:
1. A topical pharmaceutical composition for application to the skin of a subject, the pharmaceutical composition comprising:
a compound chosen from (E) isomer, (Z) isomer, and a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (Compound (I)), or a pharmaceutically acceptable salt thereof; and
at least one pharmaceutically acceptable excipient,
wherein the composition is in a form chosen from a suspension, a solution, and combinations thereof.
2. The topical pharmaceutical composition according to Embodiment 1, wherein the composition is in the form of a suspension.
3. The topical pharmaceutical composition according to Embodiment 1, wherein the composition is a formulation chosen from a gel, ointment, and cream.
4. The topical pharmaceutical composition according to Embodiment 2, wherein the composition comprises:
a compound chosen from (E) isomer, (Z) isomer, and a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (Compound (I)), or a pharmaceutically acceptable salt thereof; and
the at least one pharmaceutical acceptable excipient comprises:
a vehicle that does not individually or in combination substantially dissolve Compound (I) or the pharmaceutically acceptable salt thereof;
a humectant and/or an emollient in order to retain Compound (I) or the pharmaceutically acceptable salt thereof on the skin;
a wetting agent in order to keep Compound (I) or the pharmaceutically acceptable salt thereof de-agglomerated; and
a thickener.
5. The topical pharmaceutical composition according to Embodiment 4, wherein Compound (I) or the pharmaceutically acceptable salt of Compound (I) is micronized.
6. The topical pharmaceutical composition according to Embodiment 4, wherein Compound (I) or the pharmaceutically acceptable salt of Compound (I) has a particle size distribution $D_{90}$ ranging from 5 and 10 microns.
7. The topical pharmaceutical composition according to any one of Embodiments 4-6, wherein:
the vehicle is chosen from water, mineral oil, and combinations thereof;
the humectant and/or emollient comprises at least one of propylene glycol, glycerin, medium chain triglycerides, and combinations thereof;
the wetting agent comprises at least one of polyethoxylated sorbitan and oleic acid (Polysorbate 80), dimethicone (polydimethylsiloxane), and combinations thereof; and
the thickener comprises at least one of a crosslinked polyacrylic acid polymer (a Carbopol® polymer), a hydrogenated castor oil, a microcrystalline wax, and combinations thereof.
8. The topical pharmaceutical composition according to any one of Embodiments 4-7, wherein the composition comprises:
about 0.1% to about 10%, by weight of Compound (I) or a pharmaceutically acceptable salt thereof;
about 0.1% to about 20%, by weight of medium-chain triglycerides;
about 0.1% to about 20%, by weight of polyethoxylated sorbitan and oleic acid (Polysorbate 80);
about 0.1% to about 20%, by weight of natural glycerin;
about 0.1% to about 45%, by weight of propylene glycol;
about 0.01% to about 0.5%, by weight of methylparaben;
about 0.01% to about 0.2%, by weight of propylparaben;
about 0.1% to about 4%, by weight of a crosslinked polyacrylic acid polymer (Carbopol® 980 polymer);
an amount of 10% (w/w) of sodium hydroxide solution to adjust the pH to about 3.5 to about 8.5; and
Q.S. to 100 of water.
9. The topical pharmaceutical composition according to Embodiment 8, wherein Compound (I) or the pharmaceutically acceptable salt thereof is present at in an amount of 0.1%, 0.5%, 2%, or 5% or 10%, by weight of the composition.
10. The topical pharmaceutical composition according to Embodiment 8 or 9, wherein the composition comprises:
about 0.1%, 0.5%, 2%, 5% or 10%, by weight of Compound (I) or a pharmaceutically acceptable salt thereof;
about 2%, by weight of medium-chain triglycerides;
about 2%, by weight of polyethoxylated sorbitan and oleic acid (Polysorbate 80); about 5%, by weight of natural glycerin;
about 10%, by weight of propylene glycol;
about 0.20%, by weight of methylparaben;
about 0.05%, by weight of propylparaben;

about 0.75%, by weight of a crosslinked polyacrylic acid polymer (Carbopol® 980);

an amount of 10% (w/w) of sodium hydroxide solution to adjust the pH to about 5.0±0.5; and Q.S. to 100 of water.

11. The topical pharmaceutical composition according to any one of Embodiments 8-10, wherein the composition is a gel formulation.

12. The topical pharmaceutical composition according to any one of Embodiments 4-6, wherein the composition comprises:

about 0.1% to about 10%, by weight of Compound (I) or a pharmaceutically acceptable salt thereof;

about 0.1% to about 20%, by weight of medium-chain triglycerides;

about 0.1% to about 20%, by weight of microcrystalline wax;

about 0.1% to about 10%, by weight of hydrogenated castor oil;

about 0.01% to about 10%, by weight of dimethicone; and

Q.S. to 100 of a mineral oil.

13. The topical pharmaceutical composition according to Embodiment 12, wherein Compound (I) or the pharmaceutically acceptable salt thereof is present in an amount of 0.1%, 0.5%, 2%, 5% or 10%, by weight of the composition.

14. The topical pharmaceutical composition according to Embodiment 12 or 13, wherein the composition comprises:

about 0.1% 0.5%, 2%, 5% or 10%, by weight of Compound (I) or a pharmaceutically acceptable salt thereof;

about 10%, by weight of medium-chain triglycerides;

about 5%, by weight of microcrystalline wax;

about 2%, by weight of hydrogenated castor oil;

about 3%, by weight of dimethicone; and

Q.S. to 100 of a mineral oil.

15. The topical pharmaceutical composition according to Embodiment 14, wherein dimethicone has a viscosity of 12500 centistokes (cSt).

16. The topical pharmaceutical composition according to any one of Embodiments 12-14, wherein the composition is an ointment formulation.

17. A topical pharmaceutical composition in the form of a cream for application to the skin of a subject, the composition comprising:

about 0.01% to about 2%, by weight of Compound (I) or a pharmaceutically acceptable salt thereof;

about 1% to about 45%, by weight of oleic acid;

about 0.1% to about 20%, by weight of glycerin;

about 0.1% to about 45%, by weight of propylene glycol;

about 0.1% to about 5%, by weight of benzyl alcohol;

about 0.1% to about 5%, by weight of high molecular weight, copolymers of acrylic acid and $C_{10}$-$C_{30}$ alkyl acrylate crosslinked with allyl pentaerythritol (a Permulen™ polymer);

an amount of 10% (w/w) of sodium hydroxide solution to adjust the pH to about 3.5 to about 8.5; and Q.S. to 100 of water.

18. The topical pharmaceutical composition of Embodiment 18, wherein the Permulen™ polymer is Permulen™ TR-1.

19. The topical pharmaceutical composition according to Embodiment 17 or 18, wherein the composition comprises:

about 0.2%, by weight of Compound (I) or a pharmaceutically acceptable salt thereof;

about 25%, by weight of oleic acid;

about 5%, by weight of glycerin;

about 5%, by weight of propylene glycol;

about 1%, by weight of benzyl alcohol;

about 0.75%, by weight of Permulen™ TR-1 polymer;

an amount of 10% (w/w) of sodium hydroxide solution to adjust the pH to about 4.5 to about 5.5; and Q.S. to 100 of water.

20. The topical pharmaceutical composition according to any one of Embodiments 1-19, wherein the compound is the free base form (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (Compound (I)).

21. The topical pharmaceutical composition according to any one of Embodiments 1-20, wherein the compound is an amorphous or a crystalline form of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (Compound (I)), or a pharmaceutically acceptable salt thereof.

22. The topical pharmaceutical composition according to Embodiment 21, wherein the crystalline form is the crystalline form I or crystalline form II of the free base (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (Compound (I)).

23. The topical pharmaceutical composition according to Embodiment 21 or 22, wherein at least 95% of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (Compound (I)) is the (E) isomer.

24. A method of treating a dermatological disorder mediated by Bruton's tyrosine kinase (BTK) in a mammal in need thereof comprising:

topically administering to the skin of the mammal the topical pharmaceutical composition according to any one of Embodiments 1-23.

25. A method of treating a dermatological disorder chosen from pemphigus vulgaris, pemphigus *foliaceus*, cutaneous lupus, cutaneous lupus erythematosus, dermatitis, discoid lupus, atopic dermatitis, bullous pemphigoid, drug related skin reaction, chronic idiopathic urticaria, chronic spontaneous urticaria, symptomatic dermographism, alopecia, alopecia areata, vitiligo, pyoderma gangrenosum, membrane pemphigoid, epidermolysis bullosa acquisita, Steven Johnson Syndrome, TEN Toxic epidermal necrolysis, drug eruptions, folliculitis decalvans, pseudofolliculitis barbae, leukocytoclastic vasculitis, hidradenitis suppurativa, palmar plantar pustulosis, Lichenoid dermatitis, dermatitis herpetiformis, rosacea, erythema of rosacea, papulopustular rosacea, neutrophilic dermatoses, chronic kidney disease associated pruritis, end stage renal disease induced pruritis, acne, mycosis fungoides, and sweet syndrome in a mammal in need thereof, comprising:

topically administering to the skin of the mammal the topical pharmaceutical composition according to any one of Embodiments 1-23.

26. The method of Embodiment 24 or 25, wherein the mammal is a human.

Example Embodiments 2

Non-limiting embodiments of the disclosure include:

1. A pharmaceutical composition comprising:

at least one compound chosen from 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and pharmaceutically acceptable salts thereof; and at least one pH dependent gelling agent, wherein the pharmaceutical composition is in the form of a gel.

2. The pharmaceutical composition of Embodiment 1, wherein the pharmaceutical composition comprises about 0.1% to about 4% by weight of the at least one pH dependent gelling agent.

3. The pharmaceutical composition of Embodiment 1 or 2, wherein the at least one pH dependent gelling agent is chosen from Carbopol® polymers.

4. The pharmaceutical composition of any one of Embodiments 1-3, wherein the at least one pH dependent gelling agent is Carbopol® 980 polymer.

5. The pharmaceutical composition of any one of Embodiments 1-4, wherein the at least one compound is at least partially suspended in the gel.

6. The pharmaceutical composition of any one of Embodiments 1-5, wherein the at least one compound is substantially suspended in the gel.

7. The pharmaceutical composition of any one of Embodiments 1-6, wherein the at least one compound is suspended in the gel.

8. The pharmaceutical composition of any one of Embodiments 1-7, further comprising at least one emollient or humectant.

9. The pharmaceutical composition of Embodiment 8, wherein the pharmaceutical composition comprises about 0.1% to about 65% by weight of the at least one emollient or humectant.

10. The pharmaceutical composition of Embodiment 8 or 9, wherein the at least one emollient or humectant is chosen from glycerin, propylene glycol, and combinations thereof.

11. The pharmaceutical composition of any one of Embodiments 8-10, wherein the at least one emollient or humectant is glycerin and propylene glycol.

12. The pharmaceutical composition of any one of Embodiments 1-11, further comprising at least one preservative.

13. The pharmaceutical composition of Embodiment 12, wherein the pharmaceutical composition comprises about 0.01% to about 0.7% by weight of the at least one preservative.

14. The pharmaceutical composition of Embodiment 12 or 13, wherein the at least one preservative is chosen from methylparaben, propylparaben, and combinations thereof.

15. The pharmaceutical composition of any one of Embodiments 12-14, wherein the at least one preservative is methylparaben and propylparaben.

16. The pharmaceutical composition of any one of Embodiments 1-15, further comprising at least one lubricity agent.

17. The pharmaceutical composition of Embodiment 16, wherein the pharmaceutical composition comprises about 0.1% to about 20% by weight of the at least one lubricity agent.

18. The pharmaceutical composition of Embodiment 16 or 17, wherein the at least one lubricity agent is chosen from medium chain triglycerides.

19. The pharmaceutical composition of any one of Embodiments 1-18, further comprising at least one wetting agent.

20. The pharmaceutical composition of Embodiment 19, wherein the pharmaceutical composition comprises about 0.1% to about 20% by weight of the at least one wetting agent.

21. The pharmaceutical composition of Embodiment 19 or 20, wherein the at least one wetting agent is polysorbate 80.

22. The pharmaceutical composition of any one of Embodiments 1-21, further comprising at least one vehicle.

23. The pharmaceutical composition of Embodiment 22, wherein the at least one vehicle is chosen from aqueous solutions.

24. The pharmaceutical composition of Embodiment 22 or 23, wherein the at least one vehicle is purified water.

25. The pharmaceutical composition of any one of Embodiments 1-24, further comprising an amount of a 10% (w/w) sodium hydroxide solution sufficient to adjust the pH of the pharmaceutical composition to a value in the range of about 3.5 to about 8.5.

26. The pharmaceutical composition of Embodiment 25, wherein the value is in the range of about 4 to about 6.

27. The pharmaceutical composition of Embodiment 25 or 26, wherein the value is in the range of about 4.5 to about 5.5.

28. The pharmaceutical composition of any one of Embodiments 25-27, wherein the value is about 5.

29. The pharmaceutical composition of Embodiment 4, wherein the pharmaceutical composition comprises:
  about 0.1% to about 20% by weight of medium chain triglycerides;
  about 0.1% to about 20% by weight of Polysorbate 80;
  about 0.1% to about 20% by weight of glycerin;
  about 0.1% to about 45% by weight of propylene glycol;
  about 0.01% to about 0.5% by weight of methylparaben;
  about 0.01% to about 0.2% by weight of propylparaben;
  about 0.1% to about 4% by weight of Carbopol® 980 polymer;
  an amount of 10% (w/w) sodium hydroxide solution sufficient to adjust the pH of the pharmaceutical composition to a value in the range of about 4 to about 6; and
  Q.S. to 100 of purified water.

30. The pharmaceutical composition of Embodiment 29, wherein the pharmaceutical composition comprises:
  about 2% by weight of medium chain triglycerides;
  about 2% by weight of Polysorbate 80;
  about 5% by weight of glycerin;
  about 10% by weight of propylene glycol;
  about 0.2% by weight of methylparaben;
  about 0.05% by weight of propylparaben;
  about 0.75% by weight of Carbopol® 980 polymer;
  an amount of 10% (w/w) sodium hydroxide solution sufficient to adjust the pH of the pharmaceutical composition to a value in the range of about 4 to about 6; and
  Q.S. to 100 of purified water.

31. A pharmaceutical composition comprising:
  at least one compound chosen from 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and pharmaceutically acceptable salts thereof; and
  at least one saturated hydrocarbon,
  wherein the pharmaceutical composition is in the form of an ointment.

32. The pharmaceutical composition of Embodiment 31, wherein the at least one saturated hydrocarbon is chosen from mineral oil, hydrogenated castor oil, and combinations thereof.

33. The pharmaceutical composition of Embodiment 31 or 32, wherein the at least one saturated hydrocarbon is mineral oil and hydrogenated castor oil.

34. The pharmaceutical composition of Embodiment 32 or 33, wherein the mineral oil is chosen from white mineral oils.

35. The pharmaceutical composition of any one of Embodiments 32-34, wherein the mineral oil is Kaydol White Mineral Oil.

36. The pharmaceutical composition of any one of Embodiments 31-35, wherein the at least one compound is at least partially suspended in the ointment.

37. The pharmaceutical composition of any one of Embodiments 31-36, wherein the at least one compound is substantially suspended in the ointment.
38. The pharmaceutical composition of any one of Embodiments 31-37, wherein the at least one compound is suspended in the ointment.
39. The pharmaceutical composition of any one of Embodiments 31-38, further comprising at least one viscosity modifier.
40. The pharmaceutical composition of Embodiment 39, wherein the pharmaceutical composition comprises about 0.1% to about 20% by weight of the at least one viscosity modifier.
41. The pharmaceutical composition of Embodiment 39 or 40, wherein the at least one viscosity modifier is microcrystalline wax.
42. The pharmaceutical composition of any one of Embodiments 31-41, further comprising at least one dispersing agent.
43. The pharmaceutical composition of Embodiment 42, wherein the pharmaceutical composition comprises about 0.01% to about 30% by weight of the at least one dispersing agent.
44. The pharmaceutical composition of Embodiment 42 or 43, wherein the at least one dispersing agent is chosen from dimethicone, medium chain triglycerides, and combinations thereof.
45. The pharmaceutical composition of any one of Embodiments 42-44, wherein the at least one dispersing agent is dimethicone and medium chain triglycerides.
46. The pharmaceutical composition of Embodiment 44 or 45, wherein the dimethicone has a viscosity of 12500 centistokes (cSt).
47. The pharmaceutical composition of Embodiment 32, wherein the pharmaceutical composition comprises:
  about 0.1% to about 20% by weight of medium chain triglycerides;
  about 0.1% to about 20% by weight of microcrystalline wax;
  about 0.1% to about 10% by weight of hydrogenated castor oil;
  about 0.01% to about 10% by weight of dimethicone; and
  Q.S. to 100 of white mineral oil.
48. The pharmaceutical composition of Embodiment 47, wherein the pharmaceutical composition comprises:
  about 10% by weight of medium chain triglycerides;
  about 5% by weight of microcrystalline wax;
  about 2% by weight of hydrogenated castor oil;
  about 3% by weight of dimethicone; and
  Q.S. to 100 of white mineral oil.
49. A pharmaceutical composition comprising:
  at least one compound chosen from 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and pharmaceutically acceptable salts thereof; and
  at least one dissolution agent,
  wherein the pharmaceutical composition is in the form of a cream.
50. The pharmaceutical composition of Embodiment 49, wherein the pharmaceutical composition comprises about 1% to about 45% by weight of the at least one dissolution agent.
51. The pharmaceutical composition of Embodiment 49 or 50, wherein the at least one dissolution agent is oleic acid.
52. The pharmaceutical composition of any one of Embodiments 49-51, wherein the at least one compound is at least partially dissolved in the cream.
53. The pharmaceutical composition of any one of Embodiments 49-52, wherein the at least one compound is substantially dissolved in the cream.
54. The pharmaceutical composition of any one of Embodiments 49-53, wherein the at least one compound is dissolved in the cream.
55. The pharmaceutical composition of any one of Embodiments 49-54, further comprising at least one gelling-emulsifier.
56. The pharmaceutical composition of Embodiment 55, wherein the pharmaceutical composition comprises about 0.1% to about 5% by weight of the at least one gelling-emulsifier.
57. The pharmaceutical composition of Embodiment 55 or 56, wherein the at least one gelling-emulsifier is chosen from Pemulen™ polymers.
58. The pharmaceutical composition of any one of Embodiments 55-57, wherein the at least one gelling-emulsifier is Pemulen™ TR-1.
59. The pharmaceutical composition of any one of Embodiments 49-58, further comprising at least one alcohol.
60. The pharmaceutical composition of Embodiment 59, wherein the pharmaceutical composition comprises about 0.1% to about 5% by weight of the at least one alcohol.
61. The pharmaceutical composition of Embodiment 59 or 60, wherein the at least one alcohol is benzyl alcohol.
62. The pharmaceutical composition of any one of Embodiments 49-61, further comprising at least one emollient or humectant.
63. The pharmaceutical composition of Embodiment 62, wherein the pharmaceutical composition comprises about 0.1% to about 65% by weight of the at least one emollient or humectant.
64. The pharmaceutical composition of Embodiment 62 or 63, wherein the at least one emollient or humectant is chosen from glycerin, propylene glycol, and combinations thereof.
65. The pharmaceutical composition of any one of Embodiments 62-64, wherein the at least one emollient or humectant is glycerin and propylene glycol.
66. The pharmaceutical composition of any one of Embodiments 49-65, further comprising at least one vehicle.
67. The pharmaceutical composition of Embodiment 66, wherein the at least one vehicle is chosen from aqueous solutions.
68. The pharmaceutical composition of Embodiment 66 or 67, wherein the at least one vehicle is purified water.
69. The pharmaceutical composition of any one of Embodiments 49-68, further comprising an amount of a 10% (w/w) sodium hydroxide solution sufficient to adjust the pH of the pharmaceutical composition to a value in the range of about 3.5 to about 8.5.
70. The pharmaceutical composition of Embodiment 69, wherein the value is in the range of about 4 to about 6.
71. The pharmaceutical composition of Embodiment 69 or 70, wherein the value is in the range of about 4.5 to about 5.5.
72. The pharmaceutical composition of any one of Embodiments 69-71, wherein the value is about 5.
73. The pharmaceutical composition of Embodiment 49, wherein the pharmaceutical composition comprises:
  about 1% to about 45% by weight of oleic acid;
  about 0.1% to about 20% by weight of glycerin;
  about 0.1% to about 45% by weight of propylene glycol;
  about 0.1% to about 5% by weight of benzyl alcohol;
  about 0.1% to about 5% by weight of a Pemulen™ polymer;

an amount of 10% (w/w) sodium hydroxide solution sufficient to adjust the pH to a value in the range of about 4 to about 6; and Q.S. to 100 of purified water.

74. The pharmaceutical composition of Embodiment 73, wherein the pharmaceutical composition comprises:
about 10% by weight of oleic acid;
about 5% by weight of glycerin;
about 5% by weight of propylene glycol;
about 1% by weight of benzyl alcohol;
about 0.75% by weight of a Pemulen™ polymer;
an amount of 10% (w/w) sodium hydroxide solution sufficient to adjust the pH to a value in the range of about 4 to about 6; and
Q.S. to 100 of purified water.

75. The pharmaceutical composition of any one of Embodiments 49-74, wherein the pharmaceutical composition comprises about 0.01% to about 2% by weight of the at least one compound.

76. The pharmaceutical composition of any one of Embodiments 1-74, wherein the pharmaceutical composition comprises about 0.1% to about 10% by weight of the at least one compound.

77. The pharmaceutical composition of any one of Embodiments 1-74, wherein the pharmaceutical composition comprises about 0.5% by weight of the at least one compound.

78. The pharmaceutical composition of any one of Embodiments 1-74, wherein the pharmaceutical composition comprises at least about 0.5% by weight of the at least one compound.

79. The pharmaceutical composition of any one of Embodiments 1-74, wherein the pharmaceutical composition comprises about 1% by weight of the at least one compound.

80. The pharmaceutical composition of any one of Embodiments 1-74, wherein the pharmaceutical composition comprises about 2% by weight of the at least one compound.

81. The pharmaceutical composition of any one of Embodiments 1-74, wherein the pharmaceutical composition comprises about 5% by weight of the at least one compound.

82. The pharmaceutical composition of any one of Embodiments 1-74, wherein the pharmaceutical composition comprises about 10% by weight of the at least one compound.

83. The pharmaceutical composition of any one of Embodiments 1-82, wherein at least about 95% by weight of the at least one compound is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

84. The pharmaceutical composition of any one of Embodiments 1-83, wherein at least about 95% by weight of the at least one compound is an (E) isomer.

85. The pharmaceutical composition of Embodiment 83 or 84, wherein the at least one compound is substantially amorphous.

86. The pharmaceutical composition of any one of Embodiments 83-85, wherein the at least one compound is micronized.

87. The pharmaceutical composition of Embodiment 86, wherein the at least one compound has a particle size distribution $D_{90}$ in the range of about 5 to about 10 microns.

88. The pharmaceutical composition of any one of Embodiments 1-84, wherein the at least one compound is crystalline.

89. The pharmaceutical composition of any one of Embodiments 1-88, wherein the at least one compound is crystalline Form (I).

90. The pharmaceutical composition of Embodiment 89, wherein crystalline Form (I) is characterized by an X-ray powder diffractogram having a signal at at least three two-theta values chosen from 6.3±0.2, 12.6±0.2, 16.2±0.2, 17.6±0.2, 18.2±0.2, 18.4±0.2, and 22.1±0.2.

91. The pharmaceutical composition of Embodiment 89, wherein crystalline Form (I) is characterized by an X-ray powder diffractogram substantially similar to that in FIG. 1.

92. The pharmaceutical composition of any one of Embodiments 89-91, wherein crystalline Form (I) is characterized by a DSC thermogram having a peak endotherm (melting temperature) at about 177° C. to about 178° C.

93. The pharmaceutical composition of any one of Embodiments 89-92, wherein crystalline Form (I) is characterized by a DSC thermogram showing onset of melting at about 174.8° C. to about 175.2° C.

94. The pharmaceutical composition of Embodiment 89, wherein crystalline Form (I) is prepared by a process comprising:
adding methyl isobutyl ketone to amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile to form a solution;
agitating the solution to form a precipitate; and
isolating crystalline Form (I) by filtration.

95. The pharmaceutical composition of any one of Embodiments 1-88, wherein the at least one compound is crystalline Form (II).

96. The pharmaceutical composition of Embodiment 95, wherein crystalline Form (II) is characterized by an X-ray powder diffractogram having a signal at at least three two-theta values chosen from 6.3±0.2, 15.2±0.2, 16.0±0.2, 16.6±0.2, 17.7±0.2, 20.0±0.2, 24.8±0.2, and 27.5±0.2.

97. The pharmaceutical composition of Embodiment 95, wherein crystalline Form (II) is characterized by an X-ray powder diffractogram substantially similar to that in FIG. 3.

98. The pharmaceutical composition of any one of Embodiments 95-97, wherein crystalline Form (II) is characterized by a DSC thermogram having a peak endotherm (melting temperature) at about 170.0° C. to about 170.2° C.

99. The pharmaceutical composition of any one of Embodiments 95-98, wherein crystalline Form (II) is characterized by a DSC thermogram showing an onset of melting at about 167.2° C. to about 167.6° C.

100. The pharmaceutical composition of any one of Embodiments 95-99, wherein crystalline Form (II) is characterized by a mass loss of less than 1.5 wt. % between 35° C. and 220° C. by thermogravimetric analysis.

101. The pharmaceutical composition of Embodiment 95, wherein crystalline Form (II) is prepared by a process comprising:
dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in methyl t-butyl ether to form a solution;
stirring the solution to form a precipitate; and
isolating crystalline Form (II) by filtration.

102. A method of treating a dermatological disorder in a mammal in need thereof, the method comprising topically administering to at least a portion of the skin of the subject of the mammal at least one topical pharmaceutical composition of to any one of Embodiments 1-101.

103. The method of Embodiment 102, wherein the dermatological disorder is mediated by BTK.

104. The method of Embodiment 102 or 103, wherein the dermatological disorder is chosen from pemphigus vulgaris, pemphigus *foliaceus*, cutaneous lupus, cutaneous lupus erythematosus, dermatitis, discoid lupus, atopic dermatitis, bullous pemphigoid, drug related skin reaction, chronic idiopathic urticaria, chronic spontaneous urticaria, symptomatic dermographism, alopecia, alopecia areata, vitiligo, pyoderma gangrenosum, membrane pemphigoid, epidermolysis bullosa acquisita, Steven Johnson Syndrome, TEN Toxic epidermal necrolysis, drug eruptions, folliculitis decalvans, pseudofolliculitis barbae, leukocytoclastic vasculitis, hidradenitis suppurativa, palmar plantar pustulosis, Lichenoid dermatitis, dermatitis herpetiformis, rosacea, erythema of rosacea, papulopustular rosacea, neutrophilic dermatoses, chronic kidney disease associated pruritis, end stage renal disease induced pruritis, acne, mycosis fungoides, and sweet syndrome in a mammal in need thereof.

105. The method of any one of Embodiments 102-104, wherein the dermatological disorder is pemphigus vulgaris.
106. The method of any one of Embodiments 102-104, wherein the dermatological disorder is pemphigus foliaceus.
107. The method of any one of Embodiments 102-104, wherein the dermatological disorder is atopic dermatitis.
108. The method of any one of Embodiments 102-107, wherein the mammal is a human.
109. The method of any one of Embodiments 102-107, wherein the mammal is a canine.
110. The method of any one of Embodiments 102-107, wherein the mammal is a feline.
111. The method of any one of Embodiments 102-107, wherein the mammal is not a human.

Crystalline Form (I) of Compound (I)

In some embodiments, the present disclosure provides topical pharmaceutical compositions comprising crystalline Form (I) of Compound (I):

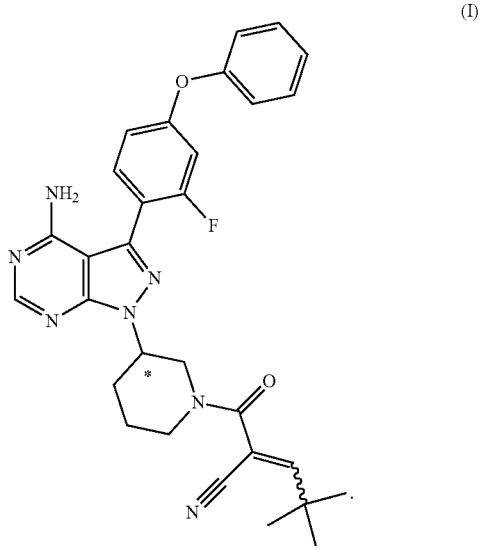 [SMILES: CC(C)(C)C=C(C#N)C(=O)N1CCCC(n2nc(-c3ccc(Oc4ccccc4)cc3F)c3c(N)ncnc32)C1]

(I)

FIG. 1 shows an X-ray powder diffractogram for crystalline Form (I) of Compound (I).

Figure 2:
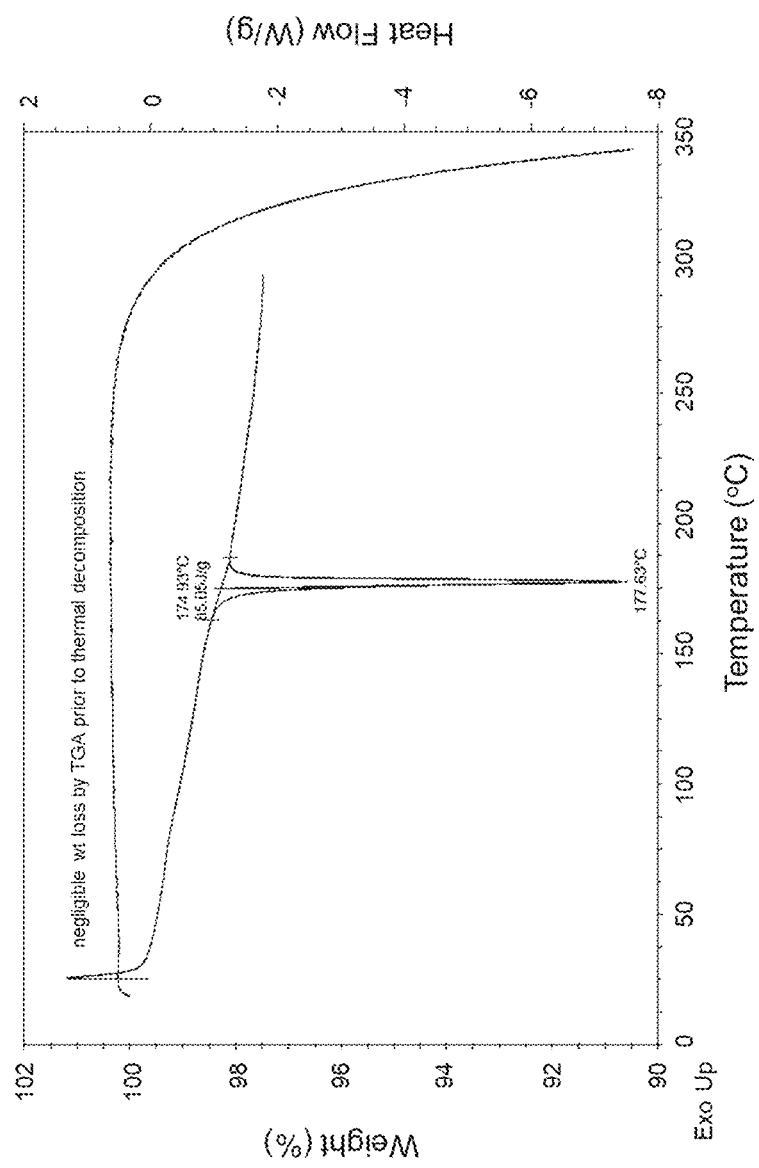
FIG. 2 shows a differential scanning calorimetry (DSC) thermogram and a thermogravimetric analysis (TGA) thermal curve for crystalline Form (I) of Compound (I).

FIG. 2 shows a DSC thermogram of crystalline Form (I) of Compound (I). In some embodiments, crystalline Form (I) of Compound (I) is characterized by a DSC thermogram having a peak endotherm (melting temperature) at about 177° C. to about 178° C. In some embodiments, crystalline Form (I) of Compound (I) is characterized by a DSC thermogram showing onset of melting/decomposition at about 174.8° C. to about 175.2° C. In some embodiments, crystalline Form (I) of Compound (I) is characterized by a DSC thermogram showing onset of melting at about 174.8° C. to about 175.2° C. In some embodiments, the associated enthalpy is about 85 J/g ($\Delta H=85$ J/g).

In some embodiments, crystalline Form (I) of Compound (I) is characterized by a DSC thermogram substantially similar to that in FIG. 2.

FIG. 2 also shows a TGA thermal curve for crystalline Form (I) of Compound (I).

In some embodiments, crystalline Form (I) of Compound (I) is a white solid.

In some embodiments, crystalline Form (I) of Compound (I) is characterized by an X-ray powder diffractogram generated by an X-ray powder diffraction analysis with an incident beam of Cu Kα radiation with signals substantially similar to those recited in Table 1.

TABLE 1

| 2-theta (deg) |
|---|
| 6.32 |
| 9.07 |
| 10.65 |
| 11.10 |
| 11.31 |
| 12.68 |
| 13.93 |
| 15.78 |
| 16.28 |
| 17.19 |
| 17.65 |
| 18.43 |
| 19.04 |
| 19.38 |
| 19.99 |
| 20.58 |
| 21.17 |
| 21.55 |
| 22.19 |
| 22.56 |
| 23.25 |
| 23.59 |
| 24.16 |
| 24.61 |
| 25.47 |
| 27.20 |
| 28.13 |
| 28.87 |
| 29.94 |
| 31.47 |
| 32.86 |
| 33.82 |
| 35.52 |
| 36.32 |

In some embodiments, crystalline Form (I) of Compound (I) is characterized by an X-ray powder diffractogram having a signal at 6.3±0.2 degrees two-theta. In some embodiments, crystalline Form (I) of Compound (I) is characterized by an X-ray powder diffractogram having a signal at 12.6±0.2 degrees two-theta. In some embodiments, crystalline Form (I) of Compound (I) is characterized by an X-ray powder diffractogram having a signal at 16.2±0.2 degrees two-theta. In some embodiments, crystalline Form (I) of Compound (I) is characterized by an X-ray powder diffractogram having a signal at 17.6±0.2 degrees two-theta. In some embodiments, crystalline Form (I) of Compound (I) is characterized by an X-ray powder diffractogram having a signal at 18.2±0.2 degrees two-theta. In some embodiments, crystalline Form (I) of Compound (I) is characterized by an X-ray powder diffractogram having a signal at 18.4±0.2 degrees two-theta. In some embodiments, crystalline Form (I) of Compound (I) is characterized by an X-ray powder diffractogram having a signal at 22.1±0.2 degrees two-theta.

In some embodiments, crystalline Form (I) of Compound (I) is characterized by an X-ray powder diffractogram having a signal at two-theta values of 6.3±0.2, 12.6±0.2, 16.2±0.2, 17.6±0.2, 18.2±0.2, 18.4±0.2, and 22.1±0.2. In some embodiments, crystalline Form (I) of Compound (I) is characterized by an X-ray powder diffractogram having a signal at at least six two-theta values chosen from 6.3±0.2, 12.6±0.2, 16.2±0.2, 17.6±0.2, 18.2±0.2, 18.4±0.2, and 22.1±0.2. In some embodiments, crystalline Form (I) of Compound (I) is characterized by an X-ray powder diffractogram having a signal at at least five two-theta values chosen from 6.3±0.2, 12.6±0.2, 16.2±0.2, 17.6±0.2, 18.2±0.2, 18.4±0.2, and 22.1±0.2. In some embodiments, crystalline Form (I) of Compound (I) is characterized by an X-ray powder diffractogram having a signal at at least four two-theta values chosen from 6.3±0.2, 12.6±0.2, 16.2±0.2, 17.6±0.2, 18.2±0.2, 18.4±0.2, and 22.1±0.2. In some embodiments, crystalline Form (I) of Compound (I) is characterized by an X-ray powder diffractogram having a signal at at least three two-theta values chosen from 6.3±0.2, 12.6±0.2, 16.2±0.2, 17.6±0.2, 18.2±0.2, 18.4±0.2, and 22.1±0.2. In some embodiments, crystalline Form (I) of Compound (I) is characterized by an X-ray powder diffractogram having a signal at at least two two-theta values chosen from 6.3±0.2, 12.6±0.2, 16.2±0.2, 17.6±0.2, 18.2±0.2, 18.4±0.2, and 22.1±0.2. In some embodiments, crystalline Form (I) of Compound (I) is characterized by an X-ray powder diffractogram having a signal at at least one two-theta value chosen from 6.3±0.2, 12.6±0.2, 16.2±0.2, 17.6±0.2, 18.2±0.2, 18.4±0.2, and 22.1±0.2.

In some embodiments, crystalline Form (I) of Compound (I) is characterized by an X-ray powder diffractogram substantially similar to that in FIG. 1.

In some embodiments, topical pharmaceutical compositions comprise crystalline Form (I) of Compound (I) prepared by a process comprising: adding methyl isobutyl ketone to amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile to form a solution. In some embodiments, the process further comprises agitating the solution to form a precipitate. In some embodiments, the process further comprises isolating crystalline Form (I) by filtration.

A method of making crystalline Form (I) of Compound (I) is disclosed in Example 1.

Crystalline Form II of Compound (I)

In some embodiments, the present disclosure provides topical pharmaceutical compositions comprising crystalline Form (II) of Compound (I):

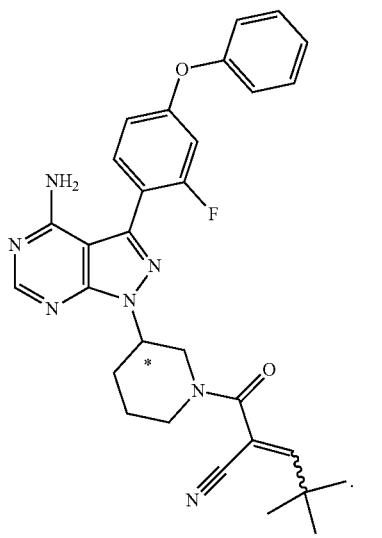

(I)

Figure 3:
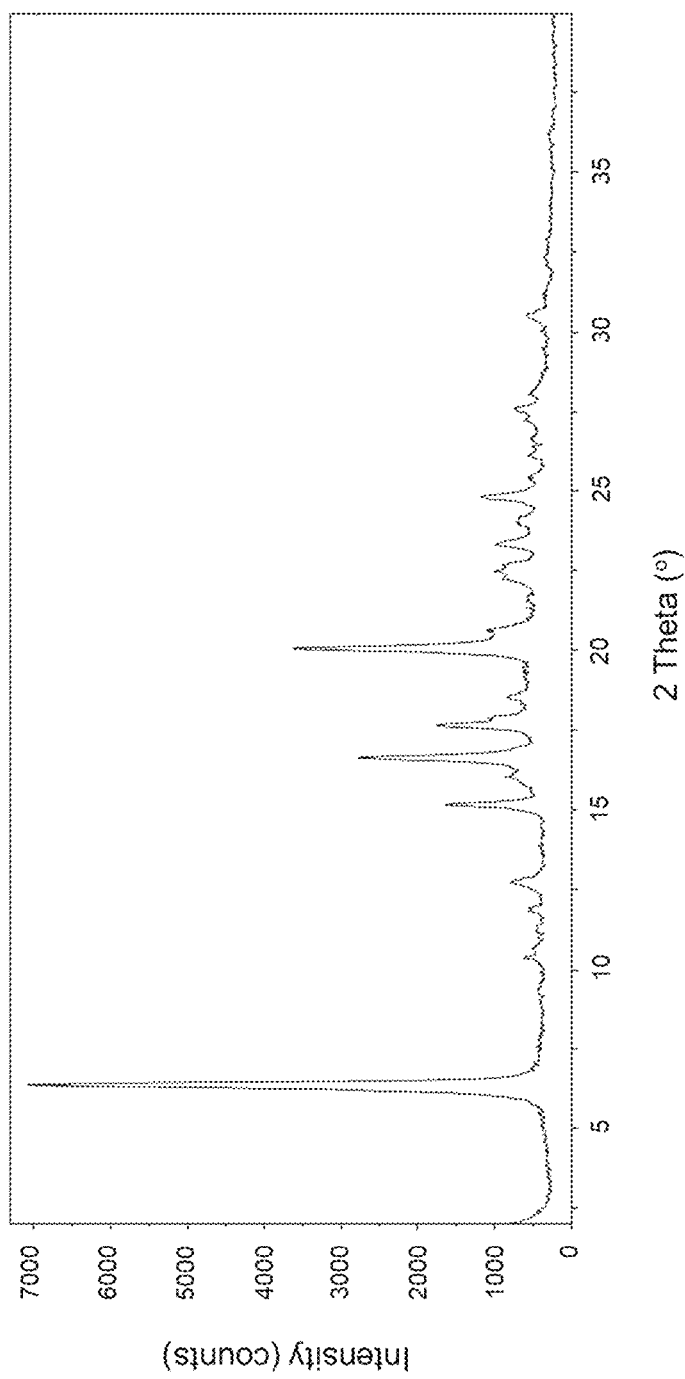
FIG. 3 shows an X-ray powder diffractogram for crystalline Form (II) of Compound (I), referred to as crystalline Form (II) herein, showing degrees 2θ (2-theta) on the X-axis and relative intensity on the Y-axis.

FIG. 3 shows an X-ray powder diffractogram for crystalline Form (II) of Compound (I).

Figure 4:
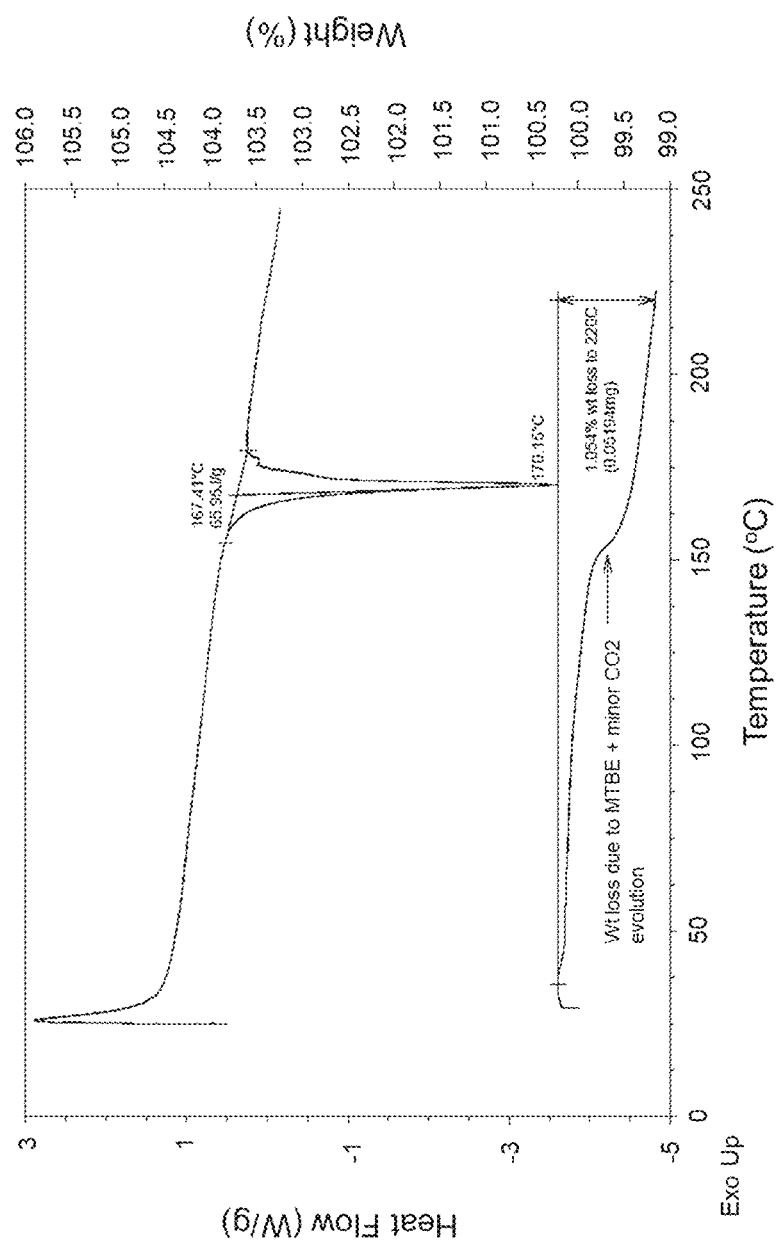
FIG. 4 shows a differential scanning calorimetry (DSC) thermogram and a thermogravimetric analysis (TGA) thermal curve for crystalline Form (II) of Compound (I).

FIG. 4 shows a DSC thermogram of crystalline Form (II) of Compound (I). In some embodiments, crystalline Form (II) of Compound (I) is characterized by a DSC thermogram having a peak endotherm (melting temperature) at about 170.0° C. to about 170.2° C. In some embodiments, crystalline Form (II) of Compound (I) is characterized by a DSC thermogram showing onset of melting/decomposition at about 167.2° C. to about 167.6° C. In some embodiments, the associated enthalpy is about 68 J/g (ΔH=68 J/g).

In some embodiments, crystalline Form (II) of Compound (I) is characterized by a DSC thermogram substantially similar to that in FIG. 4.

FIG. 4 also shows a TGA thermal curve for crystalline Form (II) of Compound (I). In some embodiments, crystalline Form (II) of Compound (I) is characterized by a mass loss of less than 1.5 wt. % between 35° C. and 220° C. by thermogravimetric analysis.

Crystalline Form (II) cannot be converted to crystalline Form (I) by heating and cooling.

In some embodiments, crystalline Form (II) of Compound (I) is characterized by an X-ray powder diffractogram generated by an X-ray powder diffraction analysis with an incident beam of Cu Kα radiation with signals substantially similar to those recited in Table 2.

TABLE 2

| 2-theta (deg) |
| --- |
| 6.32 |
| 8.87 |
| 9.32 |
| 10.38 |
| 10.60 |
| 11.22 |
| 11.86 |
| 12.71 |
| 15.18 |
| 16.04 |
| 16.63 |
| 16.96 |
| 17.67 |
| 17.91 |
| 18.54 |
| 19.18 |
| 20.05 |
| 20.64 |
| 21.64 |
| 22.27 |
| 22.51 |
| 22.72 |
| 23.33 |
| 24.03 |
| 24.83 |
| 25.42 |
| 26.12 |
| 26.34 |
| 26.68 |
| 27.24 |
| 27.55 |
| 28.05 |
| 28.36 |
| 29.37 |
| 30.03 |
| 30.53 |
| 32.11 |
| 32.33 |
| 34.12 |
| 36.20 |
| 39.24 |

In some embodiments, crystalline Form (II) of Compound (I) is characterized by an X-ray powder diffractogram having a signal at 6.3±0.2 degrees two-theta. In some embodiments, crystalline Form (II) of Compound (I) is characterized by an X-ray powder diffractogram having a signal at 15.2±0.2 degrees two-theta. In some embodiments, crystalline Form (II) of Compound (I) is characterized by an X-ray powder diffractogram having a signal at 16.0±0.2 degrees two-theta. In some embodiments, crystalline Form (II) of Compound (I) is characterized by an X-ray powder diffractogram having a signal at 16.6±0.2 degrees two-theta. In some embodiments, crystalline Form (II) of Compound (I) is characterized by an X-ray powder diffractogram having a signal at 17.7±0.2 degrees two-theta. In some embodiments, crystalline Form (II) of Compound (I) is characterized by an X-ray powder diffractogram having a signal at 20.0±0.2 degrees two-theta. In some embodiments, crystalline Form (II) of Compound (I) is characterized by an X-ray powder diffractogram having a signal at 24.8±0.2 degrees two-theta. In some embodiments, crystalline Form (II) of Compound (I) is characterized by an X-ray powder diffractogram having a signal at 27.5±0.2 degrees two-theta.

In some embodiments, crystalline Form (II) of Compound (I) is characterized by an X-ray powder diffractogram having a signal at two-theta values of 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least seven two-theta values chosen from 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least six two-theta values chosen from 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least five two-theta values chosen from 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least four two-theta values chosen from 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least three two-theta values chosen from 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least two two-theta values chosen from 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least one two-theta value chosen from 6.3±0.2, 15.2±0.2, 16.0±0.2, 16.6±0.2, 17.7±0.2, 20.0±0.2, 24.8±0.2, and 27.5±0.2.

In some embodiments, crystalline Form (II) of Compound (I) is characterized by an X-ray powder diffractogram substantially similar to that in FIG. 3.

In some embodiments, topical pharmaceutical compositions comprise crystalline Form (II) of Compound (I) prepared by a process comprising: dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in methyl t-butyl ether to form a solution. In some embodiments, the process further comprises stirring the solution to form a precipitate. In some embodiments, the process further comprises isolating crystalline Form (II) by filtration.

A method of making crystalline Form (II) of Compound (I) is disclosed in Example 2.

Topical Pharmaceutical Compositions

Compound (I), pharmaceutically acceptable salts thereof, and solid forms of Compound (I) (e.g., crystalline forms of Compound (I)) described herein are useful as active pharmaceutical ingredients (APIs), as well as materials for preparing topical pharmaceutical compositions that incorporate one or more pharmaceutically acceptable excipients and are suitable for administration (e.g., topical administration to skin) to mammals, such as human subjects. In some embodiments, these topical pharmaceutical compositions will be a pharmaceutical product, such as, e.g., a suspension, a solution, or a combination thereof.

In some embodiments, the present disclosure provides a topical pharmaceutical composition comprising at least one crystalline form of Compound (I). In some embodiments, the present disclosure provides a topical pharmaceutical composition comprising at least one crystalline form of Compound (I) chosen from crystalline Form (I) and crystalline Form (II). In some embodiments, the present disclosure provides a pharmaceutical composition comprising at least one crystalline form of Compound (I) and at least one pharmaceutically acceptable excipient. In some embodiments, the present disclosure provides a pharmaceutical composition comprising at least one crystalline form of Compound (I) chosen from crystalline Form (I) and crystalline Form (II) and at least one pharmaceutically acceptable excipient. Each excipient must be "pharmaceutically acceptable" in the sense of being compatible with the subject composition and its components not injurious to the patient. Except insofar as any conventional pharmaceutically acceptable excipient is incompatible with Compound (I), such as by producing any undesirable biological effect or otherwise interacting in a deleterious manner with any other component(s) of the pharmaceutically acceptable composition, its use is contemplated to be within the scope of this disclosure.

In some embodiments, the present disclosure provides a topical pharmaceutical composition comprising at least one substantially amorphous form of Compound (I). In some embodiments, the present disclosure provides a topical pharmaceutical composition comprising at least one amorphous form of Compound (I). In some embodiments, the present disclosure provides a pharmaceutical composition comprising at least one substantially amorphous form of Compound (I) and at least one pharmaceutically acceptable excipient. In some embodiments, the present disclosure provides a pharmaceutical composition comprising at least one amorphous form of Compound (I) and at least one pharmaceutically acceptable excipient.

In some embodiments, the present disclosure provides a topical pharmaceutical composition comprising at least one micronized form of Compound (I). In some embodiments, the present disclosure provides a pharmaceutical composition comprising at least one micronized form of Compound (I) and at least one pharmaceutically acceptable excipient.

In some embodiments, the topical pharmaceutical composition comprises at least one pharmaceutically acceptable excipient. Pharmaceutically acceptable excipients include, but are not limited, to different class of components, such as, vehicles, humectants, emollients, wetting agents, thickeners, fillers, surfactants, diluents, binders, glidants, lubricants and any combination thereof. Some non-limiting examples of materials which may serve as pharmaceutically acceptable excipients include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, also discloses additional non-limiting examples of pharmaceutically acceptable excipients, as well as known techniques for preparing and using the same.

Pharmaceutical compositions disclosed herein may be administered topically, especially when the target of treatment includes areas or organs readily accessible by topical application, including diseases of the eye, the skin, or the lower intestinal tract.

Topical pharmaceutical compositions may be in the form of a suitable gel, ointment, or cream.

In some embodiments, Compound (I) or a pharmaceutically acceptable salt thereof can be suspended or dissolved in at least one excipient to form an ointment. Excipients for topical administration of include, but are not limited to, mineral oil, liquid petrolatum, white petrolatum, propylene glycol, polyoxyethylene, polyoxypropylene compound, emulsifying wax, and water.

In some embodiments, topical pharmaceutical compositions comprising Compound (I) or a pharmaceutically acceptable salt thereof are in the form of a gel. In some embodiments, the gel further comprises at least one pH dependent gelling agent. In some embodiments, the at least one pH dependent gelling agent is chosen from Carbopol® polymers. In some embodiments, the Carbopol® polymer is Carbopol® 980 polymer. In some embodiments, the gel further comprises at least one preservative. In some embodiments, the at least one preservative is chosen from methylparaben, propylparaben, and combinations thereof. In some embodiments, the gel further comprises at least one wetting agent. In some embodiments, the at least one wetting agent is polysorbate 80. In some embodiments, the gel further comprises at least one emollient or humectant. In some embodiments, the at least one emollient or humectant is chosen from glycerin, propylene glycol, and combinations thereof. In some embodiments, the gel further comprises at least one lubricity agent. In some embodiments, the at least one lubricity agent is chosen from medium chain triglycerides. In some embodiments, the gel further comprises at least one vehicle. In some embodiments, the at least one vehicle is chosen from aqueous solutions. In some embodiments, the aqueous solution is purified water. In some embodiments, the at least one vehicle does not substantially dissolve Compound (I) or a pharmaceutically acceptable salt thereof.

In some embodiments, the gel comprises about 0.5% by weight of Compound (I) or the pharmaceutically acceptable salt thereof. In some embodiments, the gel comprises about 1% by weight of Compound (I) or the pharmaceutically acceptable salt thereof. In some embodiments, the gel comprises about 2% by weight of Compound (I) or the pharmaceutically acceptable salt thereof. In some embodiments, the gel comprises about 5% by weight of Compound (I) or the pharmaceutically acceptable salt thereof. In some embodiments, the gel comprises about 10% by weight of Compound (I) or the pharmaceutically acceptable salt thereof.

In some embodiments, Compound (I) or the pharmaceutically acceptable salt thereof is at least partially suspended in the gel. In some embodiments, Compound (I) or the pharmaceutically acceptable salt thereof is substantially suspended in the gel. In some embodiments, Compound (I) or the pharmaceutically acceptable salt thereof is suspended in the gel.

In some embodiments, a gel comprising Compound (I) or a pharmaceutical acceptable salt thereof further comprises at least one (e.g., 1, 2, 3, 4, 5, 6, at least 2, at least 3, at least 4, or at least 5) component chosen from:
  at least one pH dependent gelling agent;
  at least one emollient or humectant;
  at least one preservative;
  at least one lubricity agent;
  at least one wetting agent; and
  at least one vehicle.

In some embodiments, the at least one pH dependent gelling agent is chosen from Carbopol® polymers. In some embodiments, the Carbopol® polymer is Carbopol® 980 polymer. In some embodiments, the at least one emollient or humectant is chosen from glycerin, propylene glycol, and combinations thereof. In some embodiments, the at least one preservative is chosen from methylparaben, propylparaben, and combinations thereof. In some embodiments, the at least one lubricity agent is chosen from medium chain triglycerides. In some embodiments, the at least one wetting agent is polysorbate 80. In some embodiments, the gel further comprises at least one vehicle. In some embodiments, the at least one vehicle is chosen from aqueous solutions. In some embodiments, the aqueous solution is purified water.

In some embodiments, the gel comprises about 0.5% by weight of Compound (I) or the pharmaceutically acceptable salt thereof. In some embodiments, the gel comprises about 1% by weight of Compound (I) or the pharmaceutically acceptable salt thereof. In some embodiments, the gel comprises about 2% by weight of Compound (I) or the pharmaceutically acceptable salt thereof. In some embodiments, the gel comprises about 5% by weight of Compound (I) or the pharmaceutically acceptable salt thereof. In some embodiments, the gel comprises about 10% by weight of Compound (I) or the pharmaceutically acceptable salt thereof.

In some embodiments, Compound (I) or the pharmaceutically acceptable salt thereof is at least partially suspended in the gel. In some embodiments, Compound (I) or the pharmaceutically acceptable salt thereof is substantially suspended in the gel. In some embodiments, Compound (I) or the pharmaceutically acceptable salt thereof is suspended in the gel.

In some embodiments, a gel comprising Compound (I) or a pharmaceutical acceptable salt thereof further comprises:
  at least one pH dependent gelling agent;
  at least one emollient or humectant;
  at least one preservative;
  at least one lubricity agent;
  at least one wetting agent; and
  at least one vehicle.

In some embodiments, the at least one pH dependent gelling agent is chosen from Carbopol® polymers. In some embodiments, the Carbopol® polymer is Carbopol® 980 polymer. In some embodiments, the at least one emollient or humectant is chosen from glycerin, propylene glycol, and combinations thereof. In some embodiments, the at least one preservative is chosen from methylparaben, propylparaben, and combinations thereof. In some embodiments, the at least one lubricity agent is chosen from medium chain triglycerides. In some embodiments, the at least one wetting agent is polysorbate 80. In some embodiments, the gel further comprises at least one vehicle. In some embodiments, the at least one vehicle is chosen from aqueous solutions. In some embodiments, the aqueous solution is purified water.

In some embodiments, the gel comprises about 0.5% by weight of Compound (I) or the pharmaceutically acceptable salt thereof. In some embodiments, the gel comprises about 1% by weight of Compound (I) or the pharmaceutically acceptable salt thereof. In some embodiments, the gel comprises about 2% by weight of Compound (I) or the pharmaceutically acceptable salt thereof. In some embodiments, the gel comprises about 5% by weight of Compound (I) or the pharmaceutically acceptable salt thereof. In some embodiments, the gel comprises about 10% by weight of Compound (I) or the pharmaceutically acceptable salt thereof.

In some embodiments, Compound (I) or the pharmaceutically acceptable salt thereof is at least partially suspended in the gel. In some embodiments, Compound (I) or the pharmaceutically acceptable salt thereof is substantially suspended in the gel. In some embodiments, Compound (I) or the pharmaceutically acceptable salt thereof is suspended in the gel.

In some embodiments, a gel comprising Compound (I) or a pharmaceutical acceptable salt thereof further comprises:
 about 0.1% to about 4% by weight of at least one pH dependent gelling agent;
 about 0.1% to about 65% by weight of at least one emollient or humectant;
 about 0.01% to about 0.7% by weight of at least one preservative;
 about 0.1% to about 20% by weight of at least one lubricity agent;
 about 0.1% to about 20% by weight of at least one wetting agent; and
 at least one vehicle,
 wherein the gel comprises about 0.1% to about 10% by weight of Compound (I) or the pharmaceutically acceptable salt thereof.

In some embodiments, the at least one pH dependent gelling agent is chosen from Carbopol® polymers. In some embodiments, the Carbopol® polymer is Carbopol® 980 polymer. In some embodiments, the at least one emollient or humectant is chosen from glycerin, propylene glycol, and combinations thereof. In some embodiments, the at least one preservative is chosen from methylparaben, propylparaben, and combinations thereof. In some embodiments, the at least one lubricity agent is chosen from medium chain triglycerides. In some embodiments, the at least one wetting agent is polysorbate 80. In some embodiments, the gel further comprises at least one vehicle. In some embodiments, the at least one vehicle is chosen from aqueous solutions. In some embodiments, the aqueous solution is purified water.

In some embodiments, the gel comprises about 0.5% by weight of Compound (I) or the pharmaceutically acceptable salt thereof. In some embodiments, the gel comprises about 1% by weight of Compound (I) or the pharmaceutically acceptable salt thereof. In some embodiments, the gel comprises about 2% by weight of Compound (I) or the pharmaceutically acceptable salt thereof. In some embodiments, the gel comprises about 5% by weight of Compound (I) or the pharmaceutically acceptable salt thereof. In some embodiments, the gel comprises about 10% by weight of Compound (I) or the pharmaceutically acceptable salt thereof.

In some embodiments, Compound (I) or the pharmaceutically acceptable salt thereof is at least partially suspended in the gel. In some embodiments, Compound (I) or the pharmaceutically acceptable salt thereof is substantially suspended in the gel. In some embodiments, Compound (I) or the pharmaceutically acceptable salt thereof is suspended in the gel.

In some embodiments, topical pharmaceutical compositions disclosed herein can be formulated in a suitable lotion or cream comprising Compound (I) or a pharmaceutically acceptable salt thereof suspended or dissolved in at least one pharmaceutically acceptable excipient. Suitable excipients include, but are not limited to, mineral oil, sorbitan monostearate, polysorbate 60, polysorbate 80, cetyl esters wax, cetearyl alcohol, 2-octyldodecanol, benzyl alcohol, and water.

In some embodiments, topical pharmaceutical compositions comprising Compound (I) or a pharmaceutically acceptable salt thereof are in the form of an ointment. In some embodiments, the ointment further comprises at least one saturated hydrocarbon. In some embodiments, the at least one saturated hydrocarbon is chosen from mineral oil, hydrogenated castor oil, and combinations thereof. In some embodiments, the ointment further comprises at least one viscosity modifier. In some embodiments, the at least one viscosity modifier is microcrystalline wax. In some embodiments, the ointment further comprises at least one dispersing agent. In some embodiments, the at least one dispersing agent is chosen from dimethicone, medium chain triglycerides, and combinations thereof.

In some embodiments, the ointment comprises about 0.5% by weight of Compound (I) or the pharmaceutically acceptable salt thereof. In some embodiments, the ointment comprises about 1% by weight of Compound (I) or the pharmaceutically acceptable salt thereof. In some embodiments, the ointment comprises about 2% by weight of Compound (I) or the pharmaceutically acceptable salt thereof. In some embodiments, the ointment comprises about 5% by weight of Compound (I) or the pharmaceutically acceptable salt thereof. In some embodiments, the ointment comprises about 10% by weight of Compound (I) or the pharmaceutically acceptable salt thereof.

In some embodiments, Compound (I) or the pharmaceutically acceptable salt thereof is at least partially suspended in the ointment. In some embodiments, Compound (I) or the pharmaceutically acceptable salt thereof is substantially suspended in the ointment. In some embodiments, Compound (I) or the pharmaceutically acceptable salt thereof is suspended in the ointment.

In some embodiments, an ointment comprising Compound (I) or a pharmaceutical acceptable salt thereof further comprises at least one (e.g., 1, 2, 3, or at least 2) component chosen from:
 at least one saturated hydrocarbon;
 at least one viscosity modifier; and
 at least one dispersing agent.

In some embodiments, the at least one saturated hydrocarbon is chosen from mineral oil, hydrogenated castor oil, and combinations thereof. In some embodiments, the at least one viscosity modifier is microcrystalline wax. In some embodiments, the at least one dispersing agent is chosen from dimethicone, medium chain triglycerides, and combinations thereof.

In some embodiments, the ointment comprises about 0.5% by weight of Compound (I) or the pharmaceutically acceptable salt thereof. In some embodiments, the ointment comprises about 1% by weight of Compound (I) or the pharmaceutically acceptable salt thereof. In some embodiments, the ointment comprises about 2% by weight of Compound (I) or the pharmaceutically acceptable salt thereof. In some embodiments, the ointment comprises about 5% by weight of Compound (I) or the pharmaceutically acceptable salt thereof. In some embodiments, the ointment comprises about 10% by weight of Compound (I) or the pharmaceutically acceptable salt thereof.

In some embodiments, Compound (I) or the pharmaceutically acceptable salt thereof is at least partially suspended in the ointment. In some embodiments, Compound (I) or the pharmaceutically acceptable salt thereof is substantially suspended in the ointment. In some embodiments, Compound (I) or the pharmaceutically acceptable salt thereof is suspended in the ointment.

In some embodiments, an ointment comprising Compound (I) or a pharmaceutical acceptable salt thereof further comprises:
at least one saturated hydrocarbon;
at least one viscosity modifier; and
at least one dispersing agent.

In some embodiments, the at least one saturated hydrocarbon is chosen from mineral oil, hydrogenated castor oil, and combinations thereof. In some embodiments, the at least one viscosity modifier is microcrystalline wax. In some embodiments, the at least one dispersing agent is chosen from dimethicone, medium chain triglycerides, and combinations thereof.

In some embodiments, the ointment comprises about 0.5% by weight of Compound (I) or the pharmaceutically acceptable salt thereof. In some embodiments, the ointment comprises about 1% by weight of Compound (I) or the pharmaceutically acceptable salt thereof. In some embodiments, the ointment comprises about 2% by weight of Compound (I) or the pharmaceutically acceptable salt thereof. In some embodiments, the ointment comprises about 5% by weight of Compound (I) or the pharmaceutically acceptable salt thereof. In some embodiments, the ointment comprises about 10% by weight of Compound (I) or the pharmaceutically acceptable salt thereof.

In some embodiments, Compound (I) or the pharmaceutically acceptable salt thereof is at least partially suspended in the ointment. In some embodiments, Compound (I) or the pharmaceutically acceptable salt thereof is substantially suspended in the ointment. In some embodiments, Compound (I) or the pharmaceutically acceptable salt thereof is suspended in the ointment.

In some embodiments, an ointment comprising Compound (I) or a pharmaceutical acceptable salt thereof further comprises:
at least one saturated hydrocarbon;
about 0.1% to about 20% by weight of at least one viscosity modifier; and
about 0.01% to about 30% by weight of at least one dispersing agent,
wherein the ointment comprises about 0.1% to about 10% by weight of Compound (I) or the pharmaceutically acceptable salt thereof.

In some embodiments, the at least one saturated hydrocarbon is chosen from mineral oil, hydrogenated castor oil, and combinations thereof. In some embodiments, the at least one viscosity modifier is microcrystalline wax. In some embodiments, the at least one dispersing agent is chosen from dimethicone, medium chain triglycerides, and combinations thereof.

In some embodiments, the ointment comprises about 0.5% by weight of Compound (I) or the pharmaceutically acceptable salt thereof. In some embodiments, the ointment comprises about 1% by weight of Compound (I) or the pharmaceutically acceptable salt thereof. In some embodiments, the ointment comprises about 2% by weight of Compound (I) or the pharmaceutically acceptable salt thereof. In some embodiments, the ointment comprises about 5% by weight of Compound (I) or the pharmaceutically acceptable salt thereof. In some embodiments, the ointment comprises about 10% by weight of Compound (I) or the pharmaceutically acceptable salt thereof.

In some embodiments, Compound (I) or the pharmaceutically acceptable salt thereof is at least partially suspended in the ointment. In some embodiments, Compound (I) or the pharmaceutically acceptable salt thereof is substantially suspended in the ointment. In some embodiments, Compound (I) or the pharmaceutically acceptable salt thereof is suspended in the ointment.

In some embodiments, topical pharmaceutical compositions comprising Compound (I) or a pharmaceutically acceptable salt thereof are in the form of a cream. In some embodiments, the cream further comprises at least one dissolution agent. In some embodiments, the at least one dissolution agent is oleic acid. In some embodiments, the cream further comprises at least one gelling-emulsifier. In some embodiments, the at least one gelling-emulsifier is chosen from Pemulen™ polymers. In some embodiments, the Pemulen™ polymer is Pemulen™ TR-1. In some embodiments, the cream further comprises at least one alcohol. In some embodiments, the at least one alcohol is benzyl alcohol. In some embodiments, the cream further comprises at least one emollient or humectant. In some embodiments, the at least one emollient or humectant is chosen from glycerin, propylene glycol, and combinations thereof. In some embodiments, the cream further comprises at least one vehicle. In some embodiments, the at least one vehicle is chosen from aqueous solutions. In some embodiments, the aqueous solution is purified water.

In some embodiments, the cream comprises about 0.01% to about 2% by weight of Compound (I) or the pharmaceutically acceptable salt thereof.

In some embodiments, the cream comprises about 0.5% by weight of Compound (I) or the pharmaceutically acceptable salt thereof. In some embodiments, the cream comprises about 1% by weight of Compound (I) or the pharmaceutically acceptable salt thereof. In some embodiments, the cream comprises about 2% by weight of Compound (I) or the pharmaceutically acceptable salt thereof. In some embodiments, the cream comprises about 5% by weight of Compound (I) or the pharmaceutically acceptable salt thereof. In some embodiments, the cream comprises about 10% by weight of Compound (I) or the pharmaceutically acceptable salt thereof.

In some embodiments, Compound (I) or the pharmaceutically acceptable salt thereof is at least partially dissolved in the cream. In some embodiments, Compound (I) or the pharmaceutically acceptable salt thereof is substantially dissolved in the cream. In some embodiments, Compound (I) or the pharmaceutically acceptable salt thereof is dissolved in the cream.

In some embodiments, a cream comprising Compound (I) or a pharmaceutical acceptable salt thereof further comprises at least one (e.g., 1, 2, 3, 4, 5, at least 2, at least 3, or at least 4) component chosen from:
  at least one dissolution agent;
  at least one gelling-emulsifier;
  at least one alcohol;
  at least one emollient or humectant; and
  at least one vehicle.

In some embodiments, the at least one dissolution agent is oleic acid. In some embodiments, the at least one gelling-emulsifier is chosen from Pemulen™ polymers. In some embodiments, the Pemulen™ polymer is Pemulen™ TR-1. In some embodiments, the at least one alcohol is benzyl alcohol. In some embodiments, the at least one emollient or humectant is chosen from glycerin, propylene glycol, and combinations thereof. In some embodiments, the at least one vehicle is chosen from aqueous solutions. In some embodiments, the aqueous solution is purified water.

In some embodiments, the cream comprises about 0.01% to about 2% by weight of Compound (I) or the pharmaceutically acceptable salt thereof.

In some embodiments, the cream comprises about 0.5% by weight of Compound (I) or the pharmaceutically acceptable salt thereof. In some embodiments, the cream comprises about 1% by weight of Compound (I) or the pharmaceutically acceptable salt thereof. In some embodiments, the cream comprises about 2% by weight of Compound (I) or the pharmaceutically acceptable salt thereof. In some embodiments, the cream comprises about 5% by weight of Compound (I) or the pharmaceutically acceptable salt thereof. In some embodiments, the cream comprises about 10% by weight of Compound (I) or the pharmaceutically acceptable salt thereof.

In some embodiments, Compound (I) or the pharmaceutically acceptable salt thereof is at least partially dissolved in the cream. In some embodiments, Compound (I) or the pharmaceutically acceptable salt thereof is substantially dissolved in the cream. In some embodiments, Compound (I) or the pharmaceutically acceptable salt thereof is dissolved in the cream.

In some embodiments, a cream comprising Compound (I) or a pharmaceutical acceptable salt thereof further comprises:
  at least one dissolution agent;
  at least one gelling-emulsifier;
  at least one alcohol;
  at least one emollient or humectant; and
  at least one vehicle.

In some embodiments, the at least one dissolution agent is oleic acid. In some embodiments, the at least one gelling-emulsifier is chosen from Pemulen™ polymers. In some embodiments, the Pemulen™ polymer is Pemulen™ TR-1. In some embodiments, the at least one alcohol is benzyl alcohol. In some embodiments, the at least one emollient or humectant is chosen from glycerin, propylene glycol, and combinations thereof. In some embodiments, the at least one vehicle is chosen from aqueous solutions. In some embodiments, the aqueous solution is purified water.

In some embodiments, the cream comprises about 0.01% to about 2% by weight of Compound (I) or the pharmaceutically acceptable salt thereof.

In some embodiments, the cream comprises about 0.5% by weight of Compound (I) or the pharmaceutically acceptable salt thereof. In some embodiments, the cream comprises about 1% by weight of Compound (I) or the pharmaceutically acceptable salt thereof. In some embodiments, the cream comprises about 2% by weight of Compound (I) or the pharmaceutically acceptable salt thereof. In some embodiments, the cream comprises about 5% by weight of Compound (I) or the pharmaceutically acceptable salt thereof. In some embodiments, the cream comprises about 10% by weight of Compound (I) or the pharmaceutically acceptable salt thereof.

In some embodiments, Compound (I) or the pharmaceutically acceptable salt thereof is at least partially dissolved in the cream. In some embodiments, Compound (I) or the pharmaceutically acceptable salt thereof is substantially dissolved in the cream. In some embodiments, Compound (I) or the pharmaceutically acceptable salt thereof is dissolved in the cream.

In some embodiments, a cream comprising Compound (I) or a pharmaceutical acceptable salt thereof further comprises:
  about 1% to about 45% by weight of at least one dissolution agent;
  about 0.1% to about 5% by weight of at least one gelling-emulsifier;
  about 0.1% to about 5% by weight of at least one alcohol;
  about 0.1% to about 65% by weight of at least one emollient or humectant; and
  at least one vehicle,
  wherein the cream comprises about 0.01% to about 10% by weight of Compound (I) or the pharmaceutically acceptable salt thereof.

In some embodiments, the at least one dissolution agent is oleic acid. In some embodiments, the at least one gelling-emulsifier is chosen from Pemulen™ polymers. In some embodiments, the Pemulen™ polymer is Pemulen™ TR-1. In some embodiments, the at least one alcohol is benzyl alcohol. In some embodiments, the at least one emollient or humectant is chosen from glycerin, propylene glycol, and combinations thereof. In some embodiments, the at least one vehicle is chosen from aqueous solutions. In some embodiments, the aqueous solution is purified water.

In some embodiments, the cream comprises about 0.01% to about 2% by weight of Compound (I) or the pharmaceutically acceptable salt thereof.

In some embodiments, the cream comprises about 0.5% by weight of Compound (I) or the pharmaceutically acceptable salt thereof. In some embodiments, the cream comprises about 1% by weight of Compound (I) or the pharmaceutically acceptable salt thereof. In some embodiments, the cream comprises about 2% by weight of Compound (I) or the pharmaceutically acceptable salt thereof. In some embodiments, the cream comprises about 5% by weight of Compound (I) or the pharmaceutically acceptable salt thereof. In some embodiments, the cream comprises about 10% by weight of Compound (I) or the pharmaceutically acceptable salt thereof.

In some embodiments, Compound (I) or the pharmaceutically acceptable salt thereof is at least partially dissolved in the cream. In some embodiments, Compound (I) or the pharmaceutically acceptable salt thereof is substantially dissolved in the cream. In some embodiments, Compound (I) or the pharmaceutically acceptable salt thereof is dissolved in the cream.

Indications

The topical pharmaceutical compositions described herein may be useful for treating dermatological conditions mediated by BTK activity in mammals, such as dermatological disorders. In some embodiments, the topical pharmaceutical compositions may be used to treat humans or non-humans. In some embodiments, the topical pharmaceutical compositions may be used to treat a human. In some embodiments, the topical pharmaceutical compositions may be used to treat a non-human. In some embodiments, the topical pharmaceutical compositions may be used to treat a canine. In some embodiments, the topical pharmaceutical compositions may be used to treat a feline.

In some embodiments, the dermatological disorder is chosen from pemphigus vulgaris, pemphigus *foliaceus*, cutaneous lupus, cutaneous lupus erythematosus, dermatitis, discoid lupus, atopic dermatitis, bullous pemphigoid, drug related skin reaction, chronic idiopathic urticaria, alopecia, alopecia areata, vitiligo, pyoderma gangrenosum, membrane pemphigoid, epidermolysis bullosa acquisita, Steven Johnson Syndrome, TEN Toxic epidermal necrolysis, drug eruptions, folliculitis decalvans, pseudofolliculitis barbae, leukocytoclastic vasculitis, hidradenitis suppurativa, palmar plantar pustulosis, Lichenoid dermatitis, dermatitis herpetiformis, rosacea, erythema of rosacea, papulopustular rosacea, neutrophilic dermatoses, chronic kidney disease associated pruritis, end stage renal disease induced pruritis, acne, mycosis fungoides, and sweet syndrome.

In some embodiments, the dermatological disorder is chosen from pemphigus vulgaris and pemphigus *foliaceus*. In some embodiments, the dermatological disorder is pemphigus vulgaris. In some embodiments, the dermatological disorder is pemphigus *foliaceus*.

In some embodiments, the dermatological disorder is atopic dermatitis.

Dosing

In general, in the topical pharmaceutical compositions of the present disclosure, the effective dose for any particular mammal (e.g., any particular human) will depend upon a variety of factors including: the disorder treated and the severity of the disorder; the specific pharmaceutical composition employed; the age, body weight, general health, sex and diet of the mammal; the time of administration, the duration of the treatment; and like factors well known in the medical arts. Therapeutically effective amounts of Compound (I) may range, for example, from 0.01 to 500 mg per kg patient body weight per day, which can be administered in single or multiple doses. A suitable dosage level may be, for example, 0.01 to 250 mg/kg per day, 0.05 to 100 mg/kg per day, or 0.1 to 50 mg/kg per day. Within this range, in some embodiments, the dosage can be 0.05 to 0.5, 0.5 to 5, or 5 to 50 mg/kg per day.

All publications and patents mentioned herein are hereby incorporated by reference in their entirety as if each individual publication or patent was specifically and individually indicated to be incorporated by reference.

Claims or descriptions that include "or" or "and/or" between at least one members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all the group members are present in, employed in, or otherwise relevant to a given product or process.

Furthermore, the disclosure encompasses all variations, combinations, and permutations in which at least one limitation, element, clause, and descriptive term from at least one of the listed claims is introduced into another claim. For example, any claim that is dependent on another claim can be modified to include at least one limitation found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, embodiments of the disclosure or aspects of the disclosure consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

EXAMPLES

The following examples are intended to be illustrative and are not meant in any way to limit the scope of the disclosure.
General Methods:

A crystal form screen of Compound (I) was performed using multiple solvents and three different crystallization techniques to yield multiple crystalline forms of Compound (I), e.g., crystalline Form (I) and crystalline Form (II). In brief, the three different crystallization techniques were thermocycling (TC), rapidly cooling (RC), and slow evaporation (EV). To prepare crystalline forms of Compound (I) by thermocycling, slurries comprising Compound (I) were temperature-cycled between 5° C. and 40° C. for 36 hours, followed by equilibration at 25° C. for 8 hours. To prepare crystalline forms of Compound (I) through rapid cooling, clarified saturated solutions of Compound (I) were rapidly cooled from 25° C. to 4° C. and held at 4° C. for 48 hours. To prepare crystalline forms of Compound (I) by slow evaporation, solutions comprising Compound (I) were slowly evaporated for up to ten days. Solvents and solvent systems yielding crystalline Forms (I) and (II) are shown below in Table 3.

TABLE 3

| Solvent (w/v) | TC | RC | EV |
|---|---|---|---|
| Water | I | | |
| Methanol | I | | |
| 2-Methoxyethanol: Isopropyl ether (20:80) | I | | II |
| 1-Propanol | I | | II |
| Nitromethane | I | | II |
| Acetonitrile | I | | |
| Dimethyl sulfoxide: t-Butyl methyl ether (20:80) | | | |
| Acetone | I | | II |
| 2-Butanone | | I | I and II |
| Dichloromethane | | | |
| Methyl acetate: Heptane (20:80) | | | |
| 4-Methyl-2-pentanone | | | |
| Chloroform | | | |
| Ethyl acetate | I | | I and II |
| Chlorobenzene: Cyclohexane (20:80) | | | |
| Tetrahydrofuran | | | |
| 1,4-Dioxane | | | |
| Isopropyl ether | II | | |
| Toluene | | | II |
| Cyclohexane | II | | |
| Heptane | II | | |
| 1-Butanol | I and II | | II |
| 2-Propanol | | | |

TABLE 3-continued

| Solvent (w/v) | TC | RC | EV |
|---|---|---|---|
| Trifluoroethanol: Isopropyl ether (20:80) | II | | |
| Butyl Acetate | I | | |
| t-Butyl methyl ether | II | | |
| Isopropyl acetate | I | | II |
| Ethanol | I | | II |
| 1-Methoxy-2-propanol: Isopropyl ether (20:80) | I and II | | II |
| Cyclohexanone | | | |
| N,N-Dimethylformamide: Water (20:80) | II | | |
| 2-Methoxyethyl ether: Heptane (20:80) | II | | |
| Cyclopentyl methyl ether | I | | II |
| Acetonitrile: Water (95:5) | I | | I and II |
| Acetone: Water (95:5) | I | | II |
| Tetrahydrofuran: Water (95:5) | | | |
| 2-propanol: Water (95:5) | I | | |
| Methanol: Water (90:10) | I | | II |
| Acetonitrile: Water (90:10) | I | | II |
| Acetone: Water (90:10) | I | | II |
| 2-Me-THF | | | II |
| 1,4-Dioxane: Water (90:10) | | | |
| 2-propanol: Water (90:10) | I | | |
| Acetone: Water (80:20) | I | | |
| Ethanol: Water (20:80) | I | | |
| Ethyl acetate: Cyclohexane (20:80) | II | | |
| Acetonitrile: Isopropyl ethyl ether (20:80) | I | | |
| 4-Methyl-2-pentanone: Heptane (20:80) | II | | |

Example 1: Preparation of Crystalline Form I of Compound (I)

Methyl isobutyl ketone (MIBK; 6 mL) was added to amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (1.0 g) and stirred to form a solution. After approximately five minutes of agitation, a precipitate began to form. Additional MIBK (10 mL) was charged, and the slurry was stirred. After approximately ten days, the solid was filtered and rinsed with MIBK (10 mL). The solid was dried under vacuum with heating to afford approximately 0.5 g of crystalline form (I) of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile as a white solid. XRPD (2-Theta): 12.6, 15.7, 16.2, 18.3, 18.4, 22.1; DSC: onset 175° C., melt 177.6° C.

Example 2: Preparation of Crystalline Form II of Compound (I)

Amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (1.0 g) was dissolved in methyl t-butyl ether (MTBE, 4 mL). The solution was stirred at room temperature. After approximately 5 minutes, precipitates began to form. The slurry was charged an additional MTBE (approximately 10 mL). The solid was filtered and dried under vacuum to give approximately 0.7 g of crystalline form II of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile. XRPD (2-Theta): 15.2, 16.6, 17.6, 20.0, 24.8; DSC: onset 167° C., melt 170° C.

Example 3: Rat Arthus Study

An IgG-mediated acute Arthus rat model was employed as an in vivo pharmacologic screen, with commerically available betamethasone used as a control. Two endpoints were evaluated: (1) measurement of dye diameter after dosing; and (2) density measurement after dosing.

30 SD female rats (120-130 g) were received, individually housed, and quarantined. Rat ears were notched on the rats for identification purposes. Following quarantine, rats selected for the study were assigned to six groups of five rats each; each group had approximately the same average weight.

On day −1, the backs of the rats were shaved, and on day 0, rat weights were recorded. Three hours prior to anesthetization and intradermal injection with rabbit anti-ovalbumin IgG (T=−3 hours), the rats were fitted with Elizabethan collars and dosed topically using Carbopol gel suspensions comprising Compound (I), as in shown in Table 4 below. At T=−20 minutes, the rats were injected intravenously with 10 mg/kg ovalbumin in phosphate buffered saline (PBS) and 2% Evans Blue Dye (EBD) [2 mL/kg].

TABLE 4

Treatment Groups

| GROUP | NUMBER OF RATS | TREATMENT | DOSE (VOLUME) |
|---|---|---|---|
| 1 | 5 | Naïve | n/a |
| 2 | 5 | Gel vehicle | 100 mg/site |
| 3 | 5 | Betamethasone (0.05%) | 80 mg/site |
| 4 | 5 | 2% Compound (I) gel | 100 mg/site |
| 5 | 5 | 1% Compound (I) gel | 100 mg/site |
| 6 | 5 | 0.5% Compound (I) gel | 100 mg/site |

At T=0, the rats in the study were anesthetized and injected intradermally with rabbit anti-ovalbumin IgG (50 µg in 25 µL) in three different sites on one side of the back and with isotype rabbit IgG in three different sites on the contra-lateral side of the back. After 4 hours, the rats were euthanized, the skin was removed from the rats' backs and reversed. The diameter of the EBD leakage was measured for area calculations, and a biopsy punch biopsy (approximately 8 mm) centered around the injection site was incubated overnight at 80° C. in 2 mL formamide and EBD measured at $OD_{610\ nm}$. Suspension gel topical pharmaceutical formulations showed promising results in this study.

Promising results were also observed at extended time-points in a 16-hour prior to antibody challenge study (multiday dosing study). In a one-day dosing study, the topical formulation showed steroid-like efficacy with 1% Compound (I) in a gel formulation at 3 hours and 16 hours. Steroid-like efficacy were also observed in a 3-day dosing study at 3 hours and 16 hours, with 0.5% Compound (I) gel formulation favorably comparing to betamethasone after 3-day application.

Figure 5A:
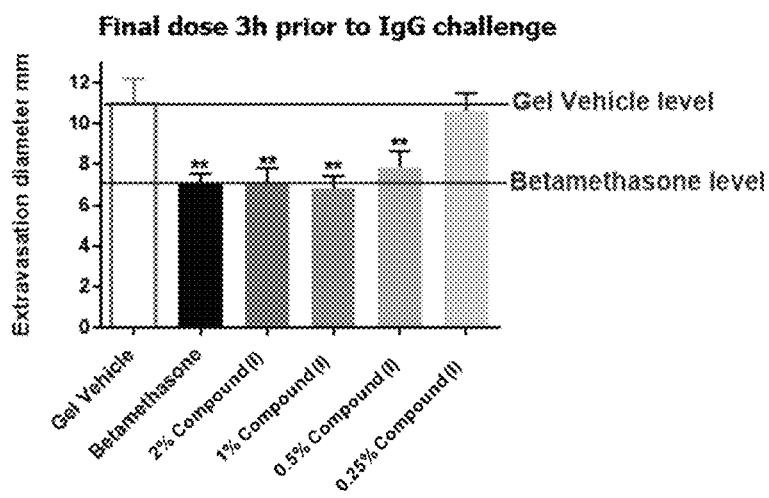
FIG. 5A and FIG. 5B depict the results of inhibition of IgG (FcgR) in a rat Arthus (macrophage/neutrophil) model employing three day dosing of gel formulations comprising Compound (I).
Figure 5B:
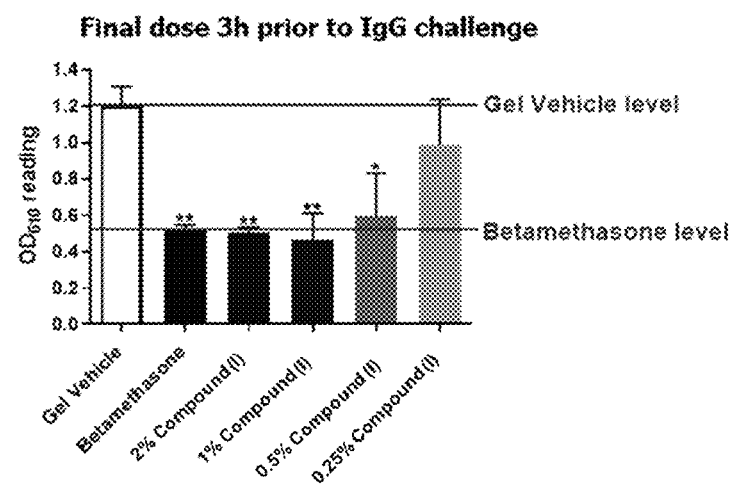

FIGS. 5A and 5B show the results of inhibition of IgG (FcgR) in the rat Arthus (macrophage/neutrophil) model at 3 hours in a 3-day dosing study. The data show that a suspension gel topical pharmaceutical formulation of the present disclosure provides steroid-like efficacy with ≥0.5% Compound (I) in a gel formulation following multiday dosing with the final dose at 3 h prior to IgG challenge.

Figure 6A:
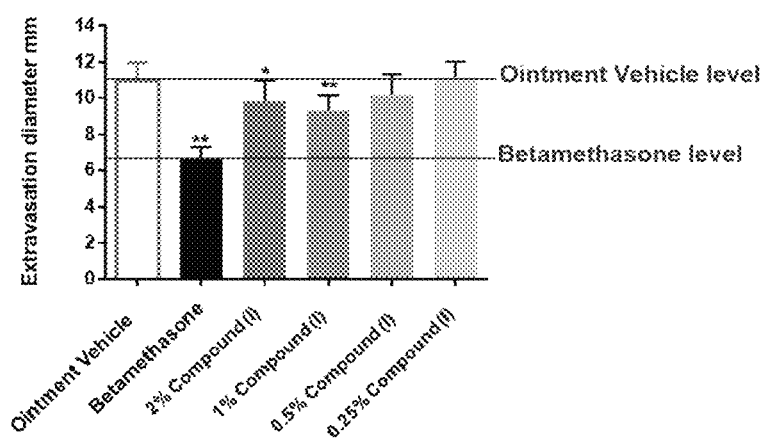
FIG. 6A and FIG. 6B depict the results of inhibition of IgG (FcgR) in a rat Arthus (macrophage/neutrophil) model employing one day dosing of ointment formulations comprising Compound (I).
Figure 6B:
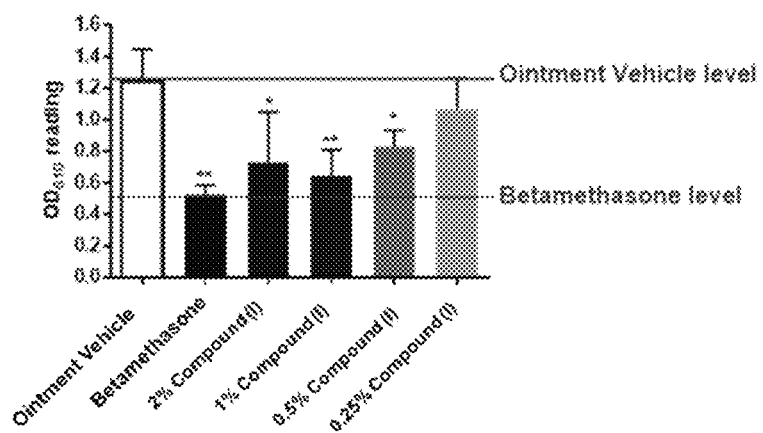
Figure 7A:
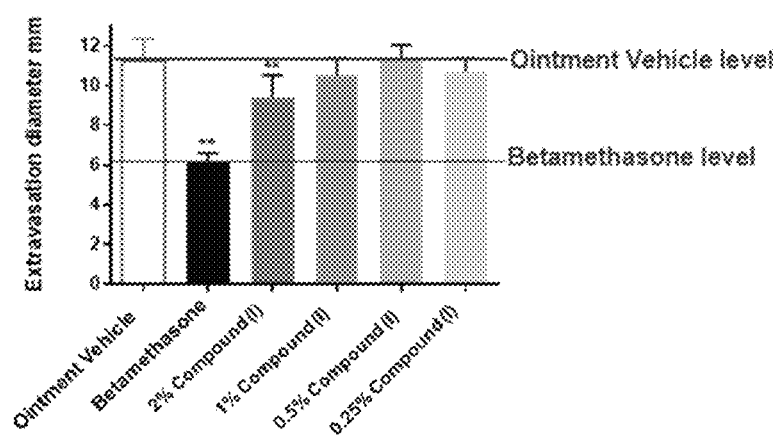
FIG. 7A and FIG. 7B depict the results of inhibition of IgG (FcgR) in a rat Arthus (macrophage/neutrophil) model employing three day dosing of ointment formulations comprising Compound (I).
Figure 7B:
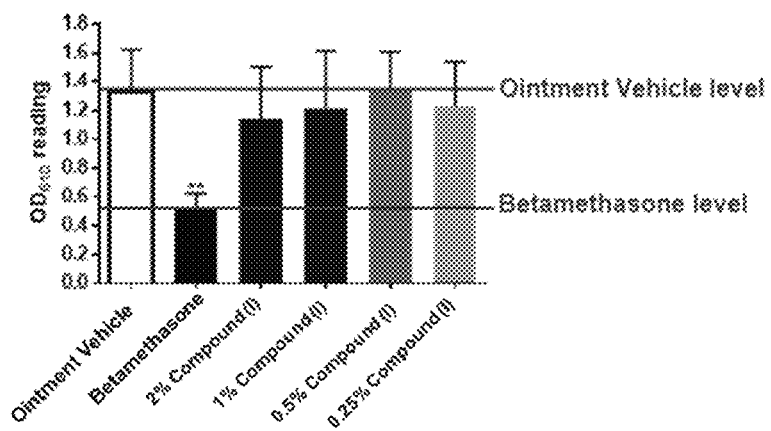

The IgG-mediated acute Arthus rat model was also used to screen certain ointment suspensions of Compound (I). FIGS. 6A and 6B show the ointment suspension study results in a 1-day dosing study, while FIGS. 7A and 7B show the ointment suspension results in a 3-day dosing study.

Example 4: Skin Penetration of Compound (I) into the Dermis and Epidermis

Compound (I) is able to penetrate human abdominal skin from elective surgery (500±50 µm) into the dermis and epidermis. Using skin from one donor (n=4-5 replicates per condition) and a receptor solution comprising phosphate/citrate buffer pH 5.6 with 0.01% Brij 98, a dose of 10 mg/cm$^2$ Compound (I) was applied in the form of one of three 2% Compound (I) gel formulations comprising one of crystalline Form (I), amorphous Compound (I), or crystalline Form (II). Samples were collected every 3 hours for 24 hours. Prior to separating the epidermis and dermis, the residual formulation was removed from the surface of the skin, and then the skin surface was tape stripped up to 5 times to remove residual formulation and the top of the skin surface layers (stratum corneum). The dermis and epidermis were separated by heating to 60° C. for 2 minutes, followed by manual separation using forceps. The extraction fluid used was 90:10 acetonitrile:water with 0.1% BHT. Epidermis and dermis samples were homogenized, then shaken at 130 RPM overnight, and transferred to lo-bind DW96 plates.

Figure 8:
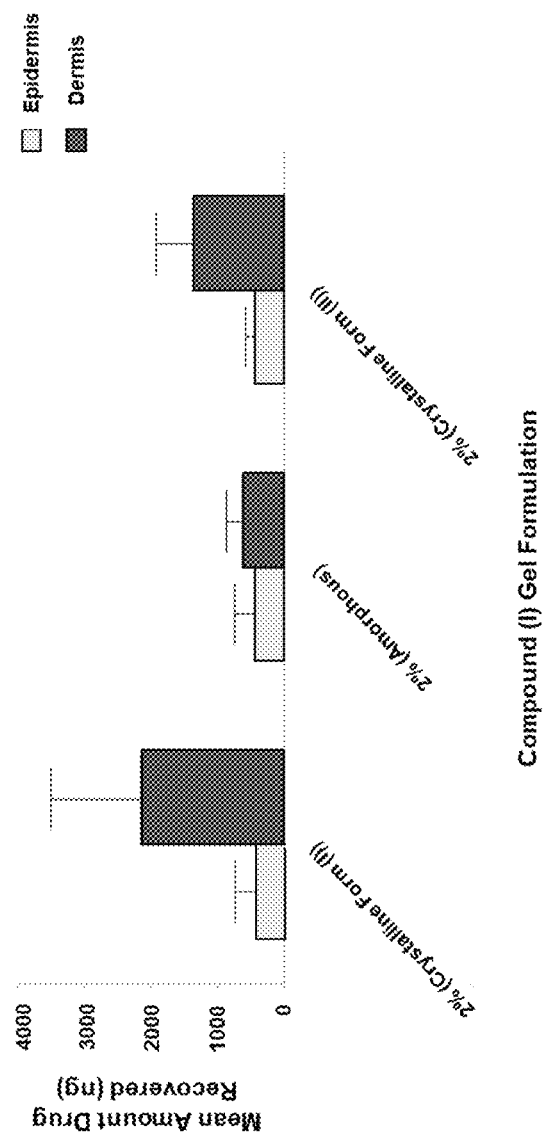
FIG. 8 depicts graphically the mean amount of Compound (I) (ng) delivered to the epidermis and dermis 24 h post-application of three 2% formulation variants using crystalline Form (I) of Compound (I), amorphous Compound (I), and crystalline Form (II) of Compound (I). Data points represent the cumulative amount of Compound (I) from 5 replicates per 1 donor (n=4-5). Error bars represent one standard deviation. Statistical outliers were removed.

Table 5 and FIG. 8 show the mean amount of Compound (I) (ng) delivered to the epidermis and dermis 24 hours post-application of three 2% formulation variants comprising one of crystalline Form (I) of Compound (I), amorphous Compound (I), or crystalline Form (II) of Compound (I). No significant differences in skin penetration ability were seen between the different formulations comprising the different forms of Compound (I) (two crystalline forms and an amorphous form), even though Compound (I) was in the form of a suspension.

TABLE 5

Mean Amount of Compound (I) 24 Hours Post-Application

| Formulation | Epidermis (ng) | | | Dermis (ng) | | |
|---|---|---|---|---|---|---|
| | N | Mean | Std Dev | N | Mean | Std Dev |
| 2% Compound (I) gel (with crystalline Form (I)) | 5 | 434 | 304 | 5 | 2159 | 1345 |
| 2% Compound (I) gel (with amorphous Compound (I)) | 4 | 450 | 297 | 4 | 636 | 232 |
| 2% Compound (I) gel (with crystalline Form (II)) | 4 | 441 | 140 | 5 | 1370 | 556 |

Example 5: Example Carbopol Gel Suspension

An example of a formulation comprising Compound (I) and Carbopol in the form of a gel suspension was prepared as shown in Table 6 below. Carbopol is a synthetic high molecular weight polymer of acrylic acid that acts as a pH dependent gelling agent.

TABLE 6

| Ingredients | % w/w |
|---|---|
| Compound (I) | 0.2-2 |
| Propylene Glycol | 10.0 |
| Methylparaben | 0.2 |
| Propylparaben | 0.05 |
| Medium Chain Triglycerides | 2.0 |
| Glycerin | 5.0 |
| Polysorbate 80 | 2.0 |
| Carbopol | 0.75 |
| 10% Sodium Hydroxide | Adjust pH to 4.5-5.5 |
| Purified Water | Q.S. to 100 |

Methylparaben and propylparaben were added as preservatives. Propylene glycol acted as a good solvent to dissolve the preservatives. Polysorbate 80 acts as a wetting agent to help with Compound (I) deagglomeration, which is typical in a suspension. Medium chain triglyceride was added as a lubricity agent, while glycerin and propylene glycol were added as skin humectants.

Example 6: Example Ointment Suspension

An example of a formulation comprising Compound (I) in the form of an ointment suspension is shown in Table 7 below.

TABLE 7

| Ingredients | % w/w |
|---|---|
| Compound (I) | 0.2-2 |
| Medium Chain Triglycerides | 10.0 |
| Microcrystalline Wax | 5 |
| Hydrogenated Castor Oil | 2.0 |
| Dimethicone | 3.0 |
| Mineral Oil | Q.S. to 100 |

A mineral oil/hydrogenated caster oil suspension of Compound (I) exhibited superior high temperature suspendability characteristics. Dimethicone and medium chain triglycerides were added for Compound (I) dispersion, while microcrystalline wax was added as a viscosity modifier.

Example 7: Example Cream Formulation

An example of a formulation comprising Compound (I) in the form of a dissolved cream is shown in Table 8 below. Pemulen™ TR-1 was chosen as a gelling-emulsifier of the cream formulation so the product could be manufactured at room temperature to avoid potential heat caused degradation during manufacture process.

TABLE 8

| Ingredients | % w/w |
|---|---|
| Compound (I) | 0.2-2 |
| Oleic Acid | 10.0 |
| Glycerin | 5.0 |
| Propylene Glycol | 5.0 |
| Benzyl Alcohol | 1.0 |
| Pemulen™ TR-1 | 0.75 |
| 1N Sodium Hydroxide | Adjust pH to 5.5 |
| Purified Water | Q.S. to 100 |

Example 8: Stability Testing

The formulations of Tables 6-8 were manufactured and placed into scintillation vials for stability monitoring at 25° C. and 40° C. Non-micronized Compound (I) was used for stability testing. In stability testing at 25° C. and 40° C. over 2.5 months, total impurities never exceeded 1% for suspension Carbopol gels and suspension ointments comprising Compound (I).

TABLE 9

| | % Label Claim | | | | |
|---|---|---|---|---|---|
| | | T = 1 Month | | T = 2.5 month | |
| Formulation | T = 0 | 25° C. | 40° C. | 25° C. | 40° C. |
| Suspension Carbopol Gel, 2% w/w Compound (I) | 100.7 | 98.9 | 109.9 | 104.7 | 127.1 |

TABLE 9-continued

| | | % Label Claim | | | |
| --- | --- | --- | --- | --- | --- |
| | | T = 1 Month | | T = 2.5 month | |
| Formulation | T = 0 | 25° C. | 40° C. | 25° C. | 40° C. |
| Suspension Ointment, 2% w/w Compound (I) | 99.0 | 107.4 | 107.7 | 109.0 | 106.3 |
| Dissolved Cream, 0.2% w/w Compound (I) | 98.0 | 94.7 | 87.9 | 91.6 | 93.1 |

Another stability study was performed with both ointment and gel suspensions comprising micronized Compound (I). Stability data for example formulations are summarized in Table 10.

TABLE 10

| | % Label Claim | | | | | |
| --- | --- | --- | --- | --- | --- | --- |
| Form- | | T = 1 month | | T = 2 month | | T = 3 month |
| ulation | T = 0 | 25° C. | 40° C. | 25° C. | 40° C. | 25° C. | 40° C. |
| Gel, 0.3% | 104.3 | 102.8 | 100.0 | 103.0 | 97.4 | 100.2 | 85.0 |
| Gel, 5% | 105.8 | 106.3 | 103.9 | 103.9 | 108.1 | 100.8 | 98.8 |
| Ointment, 0.3% | 110.7 | 104.8 | 108.8 | 105.3 | 100.7 | 106.3 | 80.2 |
| Ointment, 5% | 104.9 | 102.7 | 103.2 | 102.7 | 100.8 | 96.3 | 95.8 |

The formulations were stable at 25° C. for 3 months, and both 5% formulations were stable at 40° C. for 3 months, with some phase separation observed between vehicle and drug particles for the ointment suspension at 40° C.

Those of ordinary skill in the art will recognize or be able to ascertain using no more than routine experimentation, many equivalents to the specific embodiments of the disclosure described herein. Such equivalents are intended to be encompassed by the following claims.

What is claimed is:

1. A pharmaceutical composition comprising:
at least one compound chosen from 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and pharmaceutically acceptable salts thereof; and
about 0.1% to about 20% by weight of medium chain triglycerides;
  about 0.1% to about 20% by weight of polyethoxylated sorbitan and oleic acid;
  about 0.1% to about 20% by weight of glycerin;
  about 0.1% to about 45% by weight of propylene glycol;
  about 0.01% to about 0.5% by weight of methylparaben;
  about 0.01% to about 0.2% by weight of propylparaben;
  about 0.1% to about 4% by weight of a crosslinked polyacrylic acid polymer;
  an amount of 10% (w/w) sodium hydroxide solution sufficient to adjust the pH of the pharmaceutical composition to a value in the range of about 4 to about 6; and
  Q.S. to 100% with purified water,
wherein the pharmaceutical composition is in the form of a gel.

2. The pharmaceutical composition of claim 1, wherein the at least one compound is suspended in the gel.

3. The pharmaceutical composition of claim 1, wherein the pharmaceutical composition comprises about 0.1% to about 10% by weight of the at least one compound.

4. The pharmaceutical composition of claim 3, wherein the pharmaceutical composition comprises about 0.5% to about 10% by weight of the at least one compound.

5. The pharmaceutical composition of claim 1 wherein at least about 95% by weight of the at least one compound is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

6. The pharmaceutical composition of claim 1, wherein at least about 95% by weight of the at least one compound is an (E) isomer.

7. The pharmaceutical composition of claim 5, wherein the at least one compound is substantially amorphous.

8. The pharmaceutical composition of claim 5, wherein the at least one compound is micronized.

9. The pharmaceutical composition of claim 1, wherein the at least one compound is crystalline.

10. The pharmaceutical composition of claim 9, wherein the at least one compound is crystalline Form (I).

11. The pharmaceutical composition of claim 9, wherein the at least one compound is crystalline Form (II).

12. A method of treating a dermatological disorder in a mammal in need thereof, the method comprising topically administering to at least a portion of the skin of the subject of the mammal at least one topical pharmaceutical composition of claim 1.

13. A pharmaceutical composition comprising:
at least one compound chosen from 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and pharmaceutically acceptable salts thereof;
  at least one pH dependent gelling agent;
  at least one emollient or humectant;
  at least one preservative;
  at least one lubricity agent;
  at least one wetting agent; and
  wherein the pharmaceutical composition is in the form of a gel.

14. The pharmaceutical composition of claim 13, wherein the pharmaceutical composition comprises about 0.1% to about 4% by weight of the at least one pH dependent gelling agent.

15. The pharmaceutical composition of claim 13, wherein the at least one pH dependent gelling agent is a crosslinked polyacrylic acid polymer.

16. The pharmaceutical composition of claim 13, wherein the at least one compound is suspended in the gel.

17. The pharmaceutical composition of claim 13, wherein the pharmaceutical composition comprises about 0.1% to about 65% by weight of the at least one emollient or humectant.

18. The pharmaceutical composition of claim 13, wherein the at least one emollient or humectant is chosen from glycerin, propylene glycol, and combinations thereof.

19. The pharmaceutical composition of claim 13, wherein the pharmaceutical composition comprises about 0.01% to about 0.7% by weight of the at least one preservative.

20. The pharmaceutical composition of claim 16, wherein the at least one preservative is chosen from methylparaben, propylparaben, and combinations thereof.

21. The pharmaceutical composition of claim 13, wherein the pharmaceutical composition comprises about 0.1% to about 20% by weight of the at least one lubricity agent.

22. The pharmaceutical composition of claim 13, wherein the at least one lubricity agent is chosen from medium chain triglycerides.

23. The pharmaceutical composition of claim 13, wherein the pharmaceutical composition comprises about 0.1% to about 20% by weight of the at least one wetting agent.

24. The pharmaceutical composition of claim 13, wherein the at least one wetting agent is polyethoxylated sorbitan and oleic acid.

25. The pharmaceutical composition of claim 13, wherein at least about 95% by weight of the at least one compound is (R)-2-(3-(4-amino-3-(2-fluoro phenoxyphenyl)-1H-pyrazolo[3,4-d]pyrimidin-1-yl)piperidine-1-carbonyl)-4,4-dimethylpent enenitrile.

26. The pharmaceutical composition of claim 13, wherein at least about 95% by weight of the at least one compound is an (E) isomer.

27. The pharmaceutical composition of claim 26, wherein the at least one compound is substantially amorphous.

28. The pharmaceutical composition of claim 27, wherein the at least one compound is micronized.

29. The pharmaceutical composition of claim 13, wherein the at least one compound is crystalline.

30. The pharmaceutical composition of claim 29, wherein the at least one compound is crystalline Form (I).

31. The pharmaceutical composition of claim 29, wherein the at least one compound is crystalline Form (II).

32. A method of treating a dermatological disorder in a mammal in need thereof, the method comprising topically administering to at least a portion of the skin of the subject of the mammal at least one topical pharmaceutical composition of claim 13.

* * * * *

UNITED STATES PATENT AND TRADEMARK OFFICE
CERTIFICATE OF CORRECTION

| | | |
|---|---|---|
| PATENT NO. | : 11,583,533 B2 | Page 1 of 1 |
| APPLICATION NO. | : 17/143384 | |
| DATED | : February 21, 2023 | |
| INVENTOR(S) | : Katherine Chu et al. | |

It is certified that error appears in the above-identified patent and that said Letters Patent is hereby corrected as shown below:

In the Claims

Claim 25, Column 45, Line 9, "(2-fluoro phenoxyphenyl)" should be --(2-fluoro-4-phenoxyphenyl)--

Signed and Sealed this
Twentieth Day of June, 2023

Katherine Kelly Vidal
*Director of the United States Patent and Trademark Office*